United States Patent
Kim et al.

(10) Patent No.: US 12,208,412 B2
(45) Date of Patent: Jan. 28, 2025

(54) MIXING MODULE USED FOR REFRIGERANT PROVIDING DEVICE

(71) Applicant: RECENSMEDICAL, INC., Ulsan (KR)

(72) Inventors: Kyungbae Kim, Suwon (KR); Daehyun Kim, Hwaseong (KR); Chulho Lee, Yongin (KR); Kyongkwan Ro, Hwaseong (KR); Boo Seong Park, Hwaseong (KR)

(73) Assignee: RecensMedical, Inc., Hwaseong-si (KR)

( * ) Notice: Subject to any disclaimer, the term of this patent is extended or adjusted under 35 U.S.C. 154(b) by 0 days.

(21) Appl. No.: 18/447,195

(22) Filed: Aug. 9, 2023

(65) Prior Publication Data

US 2024/0001383 A1    Jan. 4, 2024

Related U.S. Application Data

(63) Continuation of application No. PCT/KR2023/009075, filed on Jun. 28, 2023.

(30) Foreign Application Priority Data

Jul. 1, 2022  (KR) .................. 10-2022-0081063
Nov. 11, 2022 (KR) .................. 10-2022-0151111
(Continued)

(51) Int. Cl.
B05B 7/24    (2006.01)

(52) U.S. Cl.
CPC .................................. B05B 7/2443 (2013.01)

(58) Field of Classification Search
CPC .................................. B05B 7/244; B05B 7/24
(Continued)

(56) References Cited

U.S. PATENT DOCUMENTS 4,351,304 A * 9/1982 Schweizer ............. F02M 26/20
                                                     123/585
5,219,746 A   6/1993 Brinegar et al.
(Continued)

FOREIGN PATENT DOCUMENTS

CN    1913977 A    2/2007
CN    105435982 A  3/2016
(Continued)

OTHER PUBLICATIONS

International Search Report and Written Opinion mailed Sep. 26, 2023, for PCT/KR2023/009075.
(Continued)

*Primary Examiner* — Chee-Chong Lee
(74) *Attorney, Agent, or Firm* — Knobbe, Martens, Olson, & Bear, LLP

(57) ABSTRACT

Proposed is a laser treatment device having a cooling system, the device including a laser module which irradiates a patient's skin with a laser, a sensing unit which detects a temperature of a surface of the patient's skin before, during, or after the skin is heated by the laser, a cooling module which includes an inlet which receives a refrigerant from a refrigerant storage unit, a nozzle which sprays the refrigerant on the skin, a conduit which connects the inlet with the nozzle, an flow rate control unit which controls a spray amount of the refrigerant by using a valve which is positioned on the conduit and connects or disconnects the inlet with or from the nozzle, and a refrigerant condition control unit which applies a thermal energy to the refrigerant by using a thermoelectric element located between the flow rate control unit and the nozzle.

23 Claims, 29 Drawing Sheets

(30) Foreign Application Priority Data

Dec. 2, 2022 (KR) ........................ 10-2022-0167103
Jan. 12, 2023 (KR) ........................ 10-2023-0004860

(58) Field of Classification Search
USPC .......................................................... 239/398
See application file for complete search history.

(56) References Cited

U.S. PATENT DOCUMENTS

| | | | |
|---|---|---|---|
| 5,540,388 A * | 7/1996 | Sasao | F02M 61/06 |
| | | | 239/585.4 |
| 6,053,889 A | 4/2000 | Heinzen et al. | |
| 6,141,985 A | 11/2000 | Cluzeau et al. | |
| 6,706,438 B2 * | 3/2004 | Sahoda | F04F 5/54 |
| | | | 137/111 |
| 6,966,199 B2 * | 11/2005 | Takeuchi | F25B 41/00 |
| | | | 62/503 |
| 7,455,195 B2 | 11/2008 | Mekata | |
| 7,823,400 B2 * | 11/2010 | Oshitani | F25B 41/00 |
| | | | 62/191 |
| 7,883,026 B2 * | 2/2011 | Micheli | B05B 7/067 |
| | | | 239/296 |
| 8,287,566 B2 | 10/2012 | Leopold et al. | |
| 9,109,195 B2 | 8/2015 | Zimmermann et al. | |
| 9,285,146 B2 * | 3/2016 | Liu | F25B 49/02 |
| 2004/0102768 A1 | 5/2004 | Cluzeau et al. | |
| 2004/0222315 A1 | 11/2004 | Habatjou | |
| 2005/0018036 A1 | 1/2005 | Barron et al. | |
| 2006/0157584 A1 | 7/2006 | Nomiyama et al. | |
| 2008/0054099 A1 | 3/2008 | Giroux et al. | |
| 2008/0245895 A1 | 10/2008 | Kumono | |
| 2010/0019062 A1 | 1/2010 | Clarke | |
| 2010/0305505 A1 | 12/2010 | Ducharme et al. | |
| 2011/0060195 A1 | 3/2011 | De Noray et al. | |
| 2011/0259974 A1 | 10/2011 | Cooper et al. | |
| 2012/0067977 A1 | 3/2012 | Spiegel et al. | |
| 2013/0175363 A1 | 7/2013 | Dobias et al. | |
| 2015/0014443 A1 | 1/2015 | Albisetti | |
| 2018/0214644 A1 | 8/2018 | Plan | |
| 2020/0297983 A1 | 9/2020 | Murdeshwar et al. | |
| 2021/0228822 A1 | 7/2021 | Dunne et al. | |
| 2021/0290430 A1 | 9/2021 | Kim | |
| 2022/0133380 A1 | 5/2022 | Klever et al. | |

FOREIGN PATENT DOCUMENTS

| | | | |
|---|---|---|---|
| CN | 205095992 U | 3/2016 | |
| CN | 112469393 A | 3/2021 | |
| CN | 110013589 B | 9/2021 | |
| DE | 03108918 A1 | 9/1982 | |
| JP | 08-159634 A | 6/1996 | |
| JP | 08-215614 A | 8/1996 | |
| JP | 2003-088781 A | 3/2003 | |
| JP | 2004-261657 A | 9/2004 | |
| JP | 2004-321806 A | 11/2004 | |
| JP | 2004-323109 A | 11/2004 | |
| JP | 2005-074341 A | 3/2005 | |
| JP | 2005-249193 A | 9/2005 | |
| JP | 2007-319729 A | 12/2007 | |
| JP | 2010-051774 A | 3/2010 | |
| JP | 2011-502006 A | 1/2011 | |
| JP | 2011-092977 A | 5/2011 | |
| JP | 2013-233330 A | 11/2013 | |
| JP | 2014-039916 A | 3/2014 | |
| JP | 2014-114891 A | 6/2014 | |
| JP | 2015-178001 A | 10/2015 | |
| JP | 6170909 B2 | 7/2017 | |
| JP | 6938195 B2 | 9/2021 | |
| KR | 10-2017-0142194 A | 12/2017 | |
| KR | 10-2019-0090157 A | 8/2019 | |
| KR | 10-2019-0124969 A | 11/2019 | |
| KR | 10-2020-0070095 A | 6/2020 | |
| KR | 10-2020-0070139 A | 6/2020 | |
| KR | 20-2020-0002813 U | 12/2020 | |
| KR | 20-0493630 Y1 | 5/2021 | |
| KR | 10-2022-0008730 A | 1/2022 | |
| RU | 2252042 C1 | 5/2005 | |
| WO | WO 1998/10750 A2 | 3/1998 | |
| WO | WO 2012/144990 A1 | 10/2012 | |
| WO | WO 2013/157595 A1 | 10/2013 | |
| WO | WO 2014/159016 A1 | 10/2014 | |
| WO | WO 2015/066256 A1 | 5/2015 | |
| WO | WO 2019/016105 A1 | 1/2019 | |

OTHER PUBLICATIONS

International Search Report and Written Opinion mailed Oct. 24, 2022, for PCT/KR2022/010017.

Korean Notice of Allowance dated Mar. 26, 2024 (w/English Translation), for KR 10-2022-0081063.

Taiwanese Office Action dated Jun. 17, 2024 with English Translation, for TW 112124546.

European Extended Search Report dated Sep. 23, 2024, for EP 23757505.5.

* cited by examiner (a) 1630

1611 (b) 1613 1612

(a)

(b)

(a)

(b)

MIXING MODULE USED FOR REFRIGERANT PROVIDING DEVICE

CROSS-REFERENCE TO RELATED APPLICATIONS

The present application is a continuation of International Patent Application No. PCT/KR2023/009075, filed Jun. 28, 2023, which claims the benefit of Korean Patent Application No. 10-2023-0004860, filed Jan. 12, 2023, Korean Patent Application No. 10-2022-0167103, filed Dec. 2, 2022, Korean Patent Application No. 10-2022-0151111, filed Nov. 11, 2022, and Korean Patent Application No. 10-2022-0081063, filed Jul. 1, 2022, each of which is incorporated by reference in its entirety.

TECHNICAL FIELD

The present disclosure relates to a mixing module used for a refrigerant providing device. More particularly, the present disclosure relates to a module designed to mix and spray a composition with the refrigerant in consideration of problems that may occur due to properties of the composition.

DESCRIPTION OF THE RELATED ART

In the fields of cosmetology and medical devices, a method of spraying and effectively delivering a composition containing an active ingredient to a target has been a very important task, and research on the method is being actively conducted to this day.

When considering the temperature of the composition in effectively delivering the composition to the target, particularly, research on the technology of cooling and delivering the composition in order to improve penetration performance thereof is quite limited.

Meanwhile, as a method of lowering the temperature of the composition, there may be a method of spraying the composition with a refrigerant. At this point, stable control of the temperature of the composition, uniformity of spraying the composition, and stability of spraying the composition may be influenced depending on a structure of a module in which the composition and the refrigerant are mixed. Specifically, when the composition used has physical properties such as high viscosity, strong adhesion, or low freezing point, the importance of module structural design increases.

The present disclosure will introduce a structure of a module to efficiently mix the refrigerant and the composition, and moreover, will suggest a design direction that is desirable when considering properties of the composition.

DISCLOSURE

Technical Problem

A problem to be solved of the present disclosure is to provide a device mixing and spraying a composition including active ingredient and a refrigerant, or a method of using the same.

A problem to be solved of the present disclosure is to provide a module having a structure that is coupled to a refrigerant providing device to move a composition by a negative pressure generated by spray of a refrigerant.

A problem to be solved of the present disclosure is to provide a mixing module having a structure that induces a composition to spray stream of a refrigerant.

A problem to be solved of the present disclosure is to provide a mixing module having a structure that may spray a composition in a spiral form on spray stream of a refrigerant.

A problem to be solved of the present disclosure is to provide a mixing module having a structure facilitating inflow and circulation of external air.

The technical problem of the present disclosure is not limited to the above mentioned problems, and other problem not mentioned will be clearly understood by those skilled in the art from the description below.

Technical Solution

According to an embodiment, a module comprising: an insertion hole into which a refrigerant spray unit that sprays the refrigerant is inserted; a mixing part providing a passage through which a sprayed refrigerant move; a composition inflow part formed inner side of the mixing part and fluidly connected to a composition storing part in which a composition is stored; and a spreading film comprising a first surface in physical contact with the inner side of the mixing part where the composition inflow part is formed, a second surface directly or indirectly connected to the first surface, and a first groove allowing the composition passing through the composition inflow part to move to the second surface; when the refrigerant is sprayed into the mixing part, negative pressure is formed near the composition inflow part due to the movement of the refrigerant, so that the composition stored in the composition storing part flows into the mixing part, a mixing module is provided in which a portion of the composition passing through the composition inflow part passes through the second surface and is mixed with the sprayed refrigerant.

According to another embodiment, a module used in spray device for spraying refrigerant through refrigerant spray unit, the module comprising: a mixing part having a first end and a second end, when the module is coupled to the spray device, the first end is located closer to the spray unit of the pray device that the second end; an inlet hole formed on the inner side of the mixing part and connected to a tube through which the composition moves wherein the composition is moved from the composition accommodating part to the inner side of the mixing part through the tube; and a heat transfer member attached to and detached from the inner side of the mixing part and having a third end and a fourth end when the heat transfer member is mounted inner side of the mixing part, the third end is located closer to the spray unit of the spray device than the fourth end, wherein an inner surface of the heat transfer member defines at least a portion of a passage through which the refrigerant moves, wherein the outer surface of the heat transfer member faces the inner surface of the mixing part, wherein the heat transfer member includes at least one venthole so that external air introduced into the space between the outer surface of the heat transfer member and the inner surface of the mixing part moves from the outside to the inside of the heat transfer member, the vent hole is formed closer to the third end than the fourth end of the heat transfer member.

According to another embodiment, a module used in spray device for spraying refrigerant through refrigerant spray unit, the module comprising: a mixing part having a first end and a second end, wherein the first end is located closer to the spray unit of the spray device than the second end when the module is coupled to the spray device; an inlet hole formed on the inner surface of the mixing part and connected to a tube through which the composition moves, wherein the composition is moved from the composition accommodating part to the inner side of the mixing part through the tube; and a heat transfer member having a third end and a fourth end, wherein the heat transfer member is mounted in the mixing part so that the third end is located closer to the spray unit of the spray device than the fourth end; wherein an inner surface of the heat transfer member defines a portion of a passage through which the refrigerant moves, an outer surface of the heat transfer member faces an inner surface of the mixing part, a first length from the first end to the second end of the mixing part is longer than a second length from the third end to the fourth end of the heat transfer member, wherein the third end of the heat transfer member is spaced apart from the first end of the mixing part by a predetermined distance so that the external air introduced into the space between the outer surface of the heat transfer member and the inner surface of the mixing unit moves from the outside to the inside of the heat transfer member.

According to another embodiment, a module for mixing and spraying the refrigerant and the composition, the module comprising: a mixing part providing a mixing space in which the refrigerant and the composition are mixed; an insertion hole formed inner side of the mixing part and into which the spray unit is inserted; an inlet hole formed inner side of the mixing part and through which the composition is introduced; a guide member disposed inner side of the mixing part; wherein the guide member includes a first surface contacting the inner side of the mixing part and a second surface inclined by a predetermined first inclination angle with respect to the inlet hole, when the spraying unit is inserted into the insertion hole and the refrigerant is sprayed from the spraying unit, the composition is introduced into the mixing part through the inlet hole by negative pressure, and a portion of the composition flowing into the mixing part moves along the second surface of the guide member.

The solving means of the problems of the present disclosure are not limited to the above-described solving means and solving means which have not been mentioned may be clearly understood from the specification and the attached drawings by those skilled in the art.

Advantageous Effects

According to the embodiment, the composition at relatively low temperature is sprayed to skin, so that the penetration effect of the composition with respect to the skin can be improved.

According to the embodiment, irregular or discontinuous spray of the composition with the refrigerant can be prevented.

According to the embodiment, the composition can be evenly mixed in the refrigerant stream to be sprayed.

According to the embodiment, spray of the composition in a frozen state can be prevented.

The effect of the present disclosure is not limited to the above-mentioned effects, and other effects not mentioned will be clearly understood by those skilled in the art from the description below.

DETAILED DESCRIPTION OF THE INVENTION

Figure 1:
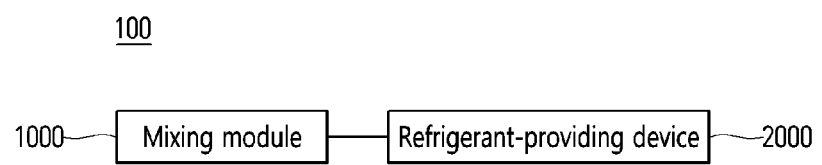
FIG. 1 is a view showing a mixture spray system according to one embodiment.

According to an embodiment, a module comprising: an insertion hole into which a refrigerant spray unit that sprays the refrigerant is inserted; a mixing part providing a passage through which a sprayed refrigerant move; a composition inflow part formed inner side of the mixing part and fluidly connected to a composition storing part in which a composition is stored; and a spreading film comprising a first surface in physical contact with the inner side of the mixing part where the composition inflow part is formed, a second surface directly or indirectly connected to the first surface, and a first groove allowing the composition passing through the composition inflow part to move to the second surface; when the refrigerant is sprayed into the mixing part, negative pressure is formed near the composition inflow part due to the movement of the refrigerant, so that the composition stored in the composition storing part flows into the mixing part, a mixing module is provided in which a portion of the composition passing through the composition inflow part passes through the second surface and is mixed with the sprayed refrigerant.

The second surface is inclined by a preset first inclination angle with respect to the inflow hole.

The spreading film includes at least the first surface, the second surface, and a first portion including the first groove.

The first part includes a third surface extending from the second surface, the mixing part has a first height in a direction perpendicular to the cross section of the inlet hole with respect to the inlet hole, and the first part has a second height with respect to the inlet hole in a direction perpendicular to the cross section of the inlet hole, and the second height is equal to or more ½ of the first height.

A first distance between the central axis of the insertion hole and the first portion is equal to or greater than ½ of a second distance between the central axis of the insertion hole and the inlet hole.

The spreading film includes a third surface physically contacting the inner surface of the mixing part, a fourth surface opposite to the third surface, and a second part that includes a second groove that allows the composition passing through the composition inflow part to move to the fourth surface.

The second surface of the first part and the fourth surface of the second part are spaced apart from each other such that a gap exists between the first part and the second part.

The inlet hole is located between the first part and the second part.

The spreading film includes a third part connecting the first part and the second part.

The third part has an arch shape, and a central axis of the third part is the same as a central axis of the insertion hole.

The mixing part is divided into a first region and a second region by the spreading film on an imaginary plane perpendicular to the central axis of the mixing part, the first region is a region corresponding to the inner side of the spreading film, and the second region is a region corresponding to the outer side of the spreading film.

A venthole is formed in at least one of the first part or the second part.

The mixing part includes a first end where the insertion hole is formed and a second end where a mixture spray hole is formed, and the vent hole is located closer to the first end than the second end.

The spreading film is made of a metal material.

The spreading film has a thermal conductivity of 12 (W/m·K) or more.

The mixing part includes a first end at which the insertion hole is formed and a second end at which a mixture spray hole is formed, wherein the spreading film extends from a first film end to a second film end in a longitudinal direction from the first end to the second end of the mixing part, wherein the first film end is closer to the insertion hole among the mixture spray hole and the insertion hole, wherein the second film end is closer to the mixture spray hole among the mixture spray hole and the insertion hole, wherein the inlet hole is located between the first end and the second end of the mixing part, wherein the second film end of the spreading film is located between the second end of the mixing part and the inlet hole.

The first surface has a first side and a second side opposite to the first side, wherein the spreading film is processed such that the first surface is curved and is located in the mixing module, wherein the first side is in physical contact with the inner surface of the mixing part.

The spreading film is processed by preparing a square plate having a first side and a second side face each other, wherein the first side is a side constituting the first surface; and curving the square plate such that the first side and the second side face each other.

According to another embodiment, a module used in spray device for spraying refrigerant through refrigerant spray unit, the module comprising: a mixing part having a first end and a second end, when the module is coupled to the spray device, the first end is located closer to the spray unit of the spray device than the second end; an inlet hole formed on the inner side of the mixing part and connected to a tube through which the composition moves wherein the composition is moved from the composition accommodating part to the inner side of the mixing part through the tube; and a heat transfer member attached to and detached from the inner side of the mixing part and having a third end and a fourth end, when the heat transfer member is mounted inner side of the mixing part, the third end is located closer to the spray unit of the spray device than the fourth end; wherein an inner surface of the heat transfer member defines at least a portion of a passage through which the refrigerant moves, wherein an outer surface of the heat transfer member opposes the inner surface of the mixing part, wherein the heat transfer member includes at least one venthole such that external air introduced into a space between the outer surface of the heat transfer member and the inner surface of the mixing part moves from the outside to the inside of the heat transfer member, wherein the vent hole is formed closer to the third end than the fourth end of the heat transfer member.

The vent hole is located between the inlet hole and the first end.

The heat transfer member includes a first part including a first surface physically contacting an inner surface of the mixing part and a second surface inclined with respect to the inlet hole by a first inclination angle.

The heat transfer member includes a second part including a third surface physically contacting an inner surface of the mixing part and a fourth surface inclined with respect to the inlet hole by a second inclination angle.

The vent hole is formed in at least one of the first part and the second part.

The inlet hole is located between the first part and the second part.

The heat transfer member includes a third part connecting the first part and the second part.

The mixing part is divided into a first region and a second region by the heat transfer member on an imaginary plane perpendicular to the central axis of the mixing part, and external air flows into the second region and moves to the first region through the vent hole.

The heat transfer member is made of a metal material.

The heat transfer member has a thermal conductivity of 12 (W/m·K) or more.

According to another embodiment, a module used in spray device for spraying refrigerant through refrigerant spray unit, the module comprising: a mixing part having a first end and a second end, wherein the first end is located closer to the spray unit of the spray device than the second end when the module is coupled to the spray device; an inlet hole formed on an inner surface of the mixing part and connected to a tube through which the composition moves, wherein the composition is moved from the composition accommodating part to an inner side of the mixing part through the tube; and a heat transfer member having a third end and a fourth end, wherein the heat transfer member is mounted in the mixing part such that the third end is located closer to the spray unit of the spray device than the fourth end; wherein the inner surface of the heat transfer member defines a portion of a passage through which the refrigerant moves, the outer surface of the heat transfer member opposes the inner surface of the mixing part, wherein a first length from the first end to the second end of the mixing part is longer than a second length from the third end to the fourth end of the heat transfer member, wherein the third end of the heat transfer member is spaced apart from the first end of the mixing part by a predetermined distance such that the external air introduced into the space between the outer surface of the heat transfer member and the inner surface of the mixing unit moves from the outside to the inside of the heat transfer member.

When viewed in a direction perpendicular to a central axis of the mixing part, a gap is formed between the third end of the heat transfer member and the first end of the mixing part.

A distance between the first end of the mixing part and the third end of the heat transfer member is greater than a distance between the second end of the mixing part and the fourth end of the heat transfer member.

According to another embodiment, a module for mixing and spraying the refrigerant and composition, the module comprising: a mixing part providing a mixing space in which the refrigerant and the composition are mixed; an insertion hole formed inner side of the mixing part and into which the spray unit is inserted; an inlet hole formed inner side of the mixing part and through which the composition is introduced; a guide member disposed inner side of the mixing part; wherein the guide member includes a first surface contacting the inner side of the mixing part and a second surface inclined by a predetermined first inclination angle with respect to the inlet hole, when the spraying unit is inserted into the insertion hole and the refrigerant is sprayed from the spraying unit, the composition is introduced into the mixing part through the inlet hole by negative pressure, and a portion of the composition flowing into the mixing part moves along the second surface of the guide member.

The guide member includes a first plate including the first surface and the second surface, and the first plate, when disposed inner side of the mixing part, has a first length in a first direction parallel to the central axis of the mixing part, and has a first height in a second direction perpendicular to the central axis of the mixing part based on the inlet hole.

When the mixing part has a first width in the second direction, the first height of the first plate is equal to or greater than ½ of the first width.

The mixing part has a second length in the first direction, and the first length is shorter than the second length.

The first plate has a first end and a second end in the first direction, wherein the first end is closer to the insertion hole than the second end, and the inlet hole is located between the first end and the second end.

The guide member includes a first plate including the first surface and the second surface, and a second plate including a third surface contacting the inner side of the mixing part and a fourth surface inclined by a predetermined second inclination angle with respect to the inlet hole, a portion of the composition flowing into the mixing part moves along the fourth surface of the guide member.

The inlet hole is located between the first plate and the second plate.

The guide member includes a third plate connecting the first plate and the second plate. The mixing part is divided into a first region into which the refrigerant is sprayed and a second region into which external air is introduced by the guide member on an imaginary plane perpendicular to the central axis of the mixing part.

The third plate has an arch shape, and a central axis of the third plate is the same as a central axis of the insertion hole.

A venthole is formed in at least one of the first plate or the second plate.

The mixing part has a first end where the insertion hole is formed and a second end where a mixture spray hole through which the refrigerant is discharged is formed, and the vent hole is located closer to the first end than the second end.

A first groove corresponding to the inlet hole is formed on the first surface, and the composition flows into the mixing part through the first groove on the first surface.

The preset angle is within 10° to 90°.

The preset angle is within 0° to 10°.

The first surface and the second surface face each other.

The guide member is made of a metal material.

The guide member has a thermal conductivity of 12 (W/m·K) or more.

The guide member is made of copper (Cu).

At least one protrusion for supporting the guide member is formed inner side of the mixing part.

According to another embodiment, a mixing module mounted on a cooling device, the module comprising: a mixing part having a shape extending from a first end to a second end; a composition inflow part fluidly connected to an inner side of the mixing part and providing a passage through which the composition stored in the composition storing part moves to the inner side of the mixing part; and a spreading film disposed the inner side of the mixing part and extending from a third end to a fourth end, wherein the spreading film is disposed adjacent to the composition inflow part such that the composition introduced through the composition inflow part is adsorbed and moved, includes a first inclined surface having an inclination with respect to the composition inflow part; when the refrigerant flows into one side of the mixing part, a negative pressure is formed in an area adjacent to the composition inflow part due to the movement of the refrigerant, such that the composition stored in the composition storing part flows into the mixing part, and a portion of the composition passing through the composition inflow part moves along the first slope and flows out to the other side of the mixing part together with the sprayed refrigerant.

The composition inflow part is fluidly connected to the inlet hole formed inner side of the mixing part to allow the composition to pass through the inlet hole, and the first inclined surface is inclined by a predetermined first inclination angle with respect to the inlet hole.

The spreading film includes a first contact surface in which the composition inflow part is fluidly connected to an inlet hole formed inside the mixing part to allow the composition to pass through the inlet hole, and physically contacts the inside of the mixing part at a point adjacent to the composition inflow part. And a first hole penetrating the first contact surface.

the spreading film is The composition inflow part is fluidly connected to an inlet hole formed inside the mixing part so that the composition passes through the inlet hole, The spreading film includes a first contact surface physically contacting the inner side of the mixing part at a point adjacent to the composition inlet unit and a first hole penetrating the first contact surface.

The mixing part has a first height in a direction perpendicular to the cross section of the inlet hole with respect to the inlet hole, the spreading film has a second height in a direction perpendicular to the cross section of the inlet hole based on the inlet hole, and the second height is equal to or higher than ½ of the first height.

A first distance between a central axis of the mixing part and the first inclined surface is equal to or greater than ½ of a second distance between a central axis of the mixing part and the inlet hole.

The spreading film includes a second inclined surface provided to adsorb and move the composition introduced through the composition inflow part, a second contact surface physically contacting the mixing part at a point adjacent to the composition inflow part, and a second hole penetrating the second contact surface, wherein the first inclined surface and the first contact surface are an integrated first spreading part, and the second inclined surface and the second contact surface are an integrated other second spreading part.

The first contact surface and the second contact surface are spaced apart from each other such that a gap through which fluid can move is formed between the first spreading part and the second spreading part.

The first hole and the second hole are disposed at positions corresponding to the inlet hole.

The spreading film includes a third spreading part connecting the first spreading part and the second spreading part and having an arch shape.

An insertion hole into which a nozzle of the cooling device is inserted is further included, the insertion hole is formed on one side of the mixing part, and a central axis of the third spreading part is the same as a central axis of the insertion hole.

The mixing part is divided into a first region and a second region by the spreading film on a virtual plane perpendicular to the central axis of the mixing part, the first region is a region corresponding to an inner side of the spreading film, and the second region is a region corresponding to an outer side of the spreading film.

A venthole is formed on at least one of the first inclined surface and the second inclined surface.

An insertion hole into which a nozzle of the cooling device is inserted is further included, the insertion hole is formed on one side of the mixing part, and the vent hole is located closer to the one side of the mixing part than to the other side of the mixing part.

The spreading film is made of a metal material.

The spreading film has a thermal conductivity of 12 (W/m·K) or more.

The spreading film may be processed by preparing a rectangular plate having a first side and a second side opposite to each other, wherein the first side is a side constituting the first inclined surface; and curving the square plate such that the first side and the second side face each other.

According to another embodiment, a mixing module mounted on a cooling device, the mixing module comprising: a mixing part having a shape extending from a first end to a second end, wherein the first end is disposed closer to the cooling device than the second end when the mixing module is mounted on the cooling device; a composition inflow part fluidly connected to an inner side of the mixing part and providing a passage through which the composition stored in the composition storing part moves to the inner side of the mixing part; and a heat transfer member disposed the inner side of the mixing part and having a shape extending from a third end to a fourth end, when the heat transfer member is mounted the inner side of the mixing part, the third end is disposed closer to the cooling device than the fourth end, and the third end is disposed closer to the first end than the second end of the mixing part; wherein the heat transfer member includes at least one vent hole formed closer to the third end of the heat transfer member than the fourth end, when the heat transfer member is disposed in the mixing part, an outer surface of the heat transfer member opposes an inner surface of the mixing part and a space is formed between the outer surface of the heat transfer member and an inner surface of the mixing part, when the refrigerant flows into the first end of the mixing part and flows out to the second end of the mixing part together with the composition, external air flowing into the space moves to the inner side of the heat transfer member through the vent hole and flows out to the second end of the mixing part.

In a first direction from the first end to the second end, the vent hole is disposed upstream compared to the composition inflow part and is disposed downstream compared to the first end.

The composition inflow part is fluidly connected to the inlet hole formed inner side of the mixing part such that the composition passes through the inlet hole, the heat transfer member includes a first contact surface physically contacting the mixing part at a point adjacent to the composition inflow part and a first inclined surface disposed inclined at a first inclination angle with respect to the inlet hole and allowing the composition to adsorb and move.

The heat transfer member includes a second contact surface physically contacting the mixing part at a point adjacent to the composition inflow part and a second inclined surface disposed inclined at a second inclination angle with respect to the inlet hole and allowing the composition to be adsorbed and moved, the first contact surface and the first inclined surface are an integral first spreading part, and the second contact surface and the second inclined surface are an integral other second spreading part.

The vent hole is formed in at least one of the first spreading part and the second spreading part.

The heat transfer member includes a first hole penetrating the first contact surface and a second hole penetrating the second contact surface, and the first hole and the second hole are disposed at positions corresponding to the inlet hole.

The mixing part has a first height in a direction perpendicular to the cross section of the inlet hole based on the inlet hole, and, in a direction perpendicular to the cross section of the inlet hole based on the inlet hole, the spreading film has a second height, and the second height is equal to or higher than ½ of the first height.

The mixing part is divided into a first region and a second region by the heat transfer member on an imaginary plane perpendicular to the central axis of the mixing part, the external air flows into the second region and moves to the first region through the vent hole.

The heat transfer member is made of a metal material.

The heat transfer member has a thermal conductivity of 12 (W/m·K) or more.

According to another embodiment, a mixing module mounted on a cooling device, the mixing module comprising: a mixing part having a shape extending from a first end to a second end, when the mixing module is mounted on the cooling device, the first end is disposed closer to the spray unit of the spray device than the second end; a composition inflow part fluidly connected to an inner side of the mixing part and providing a passage through which the composition stored in the composition storing part moves to the inner side of the mixing part; and a heat transfer member disposed the inner side of the mixing part and having a shape extending from a third end to a fourth end, wherein the third end is located closer to the cooling device than the fourth end, wherein a first length which is a straight line distance between the first and second ends of the mixing part is longer than a second length which is a straight line distance between the third end and the fourth end of the heat transfer member, when the heat transfer member is disposed in the mixing part, an outer surface of the heat transfer member faces the inner surface of the mixing part and a space is formed between the outer surface of the heat transfer member and the inner surface of the mixing part, wherein the third end of the heat transfer member is spaced apart from the first end of the mixing part by a predetermined distance, when the refrigerant flows into the first end of the mixing part and flows out to the second end of the mixing part together with the composition, an external air flowing into the space moves to an inner side of the heat transfer member through a spaced apart space and flows out to the second end of the mixing part.

A straight line distance between the first end of the mixing part and the third end of the heat transfer member is greater than a straight line distance between the second end of the mixing part and the fourth end of the heat transfer member.

The foregoing objectives, features, and advantages will become more apparent from the following detailed description taken in conjunction with the accompanying drawings. However, the present disclosure may have various changes and various embodiments, and hereinafter, specific embodiments will be illustrated in the drawings and described in detail.

In the drawings, the thickness of a layer and a region is exaggerated for clarity, and that a component or a layer is referred to as being "on" another component or another layer includes all cases in which other layers or other components are intervened in the middle as well as immediately on other components or layers. The same reference numerals are used throughout the specification to designate the same or similar components. In addition, a component having the same function within the scope of the same idea appearing in the drawings of each embodiment will be described using the same reference numerals, and overlapping descriptions thereof will be omitted.

It will be understood that, although the numbers first, second, etc. may be used to be only identifiers for distinguishing one component from another component.

In addition, the terms "module" and "unit" or components used in the following embodiments are given or used interchangeably in consideration of ease of writing the specification, and do not have meanings or roles that are distinguished from each other by themselves.

As used herein, the singular forms are intended to include the plural forms as well, unless the context clearly indicates otherwise.

It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

In these drawings, the sizes of components may be exaggerated or downscale for convenient description, and for example, in the drawings, sizes or thicknesses of components may be arbitrarily expressed for convenience of description, but the present disclosure is not limited thereto.

When an embodiment is otherwise implementable, a specific process sequence may be performed differently from the described sequence. As an example, two processes described in succession may be performed substantially simultaneously, or may proceed in an order reverse to the order described.

In the embodiments described hereinbelow, when a film, a region, a component, etc. is referred to as being connected to another film, region, component, etc., the film, the region, the component, etc. can be directly connected to the other film, region, component, etc., and connection can be indirectly achieved with other film, region, component, etc. intervening therebetween.

For example, in the specification, when a film, a region, a component, etc. is referred to as being electrically connected to another film, region, component, etc., the film, the region, the component, etc. can be electrically directly connected to another film, region, component, etc., and connection can be electrically indirectly achieved with other film, region, component, etc. intervening therebetween.

In the embodiments described hereinbelow, when a film, a region, a component, etc. is referred to as being fluidly connected to another film, region, component, etc., it may be understood that the film, the region, the component, etc. may form at least a part of a flow path through which each fluid flows.

For example, in this specification, that a component A is fluidly connected to a component B may mean that a fluid passing through a flow path formed by the component A may reach a flow path formed by the component B or vice versa. Specifically, when the component A and the component B are coupled to each other and the flow path formed by the component A and the flow path formed by the component B are directly connected to each other, the component A and the component B can be considered to be fluidly connected to each other. Otherwise, when the component A and component B are connected to each other through a component C, such as a conduit, so that the flow path formed by the component A and the flow path formed by the component B are indirectly connected to each other through a flow channel formed by the component C, the component A and component B can be seen as fluidly connected to each other. At this point, the component C can be understood as fluidly connecting the components A and B to each other. Furthermore, the component A and component B may be fluidly connected to each other through a plurality of components.

The specification relates to a mixing module used for a refrigerant providing device. The mixing module is intended to mix a composition with a refrigerant supplied from the refrigerant providing device to spray the refrigerant and the composition together. As the refrigerant and the composition are mixed together and the mixture thereof is sprayed to a target, the composition having a relatively low temperature can be sprayed to the target.

At this point, the composition has a concept including not only a pharmacological composition used for a medical treatment purpose but also a cosmetic composition used for a cosmetic purpose, and the composition may mean a material including an active ingredient inducing or generating a medical effect or a cosmetic effect.

At this point, as the refrigerant, it may be used a material that can apply cooling energy to a target area, such as carbon dioxide ($CO_2$), liquid nitrogen (LN), nitrogen dioxide ($NO_2$), nitrogen monoxide (NO), a material of the hydrofluorocarbon (HFC) family, methane ($CH_4$), PFC, $SF_6$, a coolant, a cooling gas, etc.

At this point, 'the target' may mean a body part to which procedure, treatment, or care is performed to make a cosmetic effect or a medical effect. For example, a target may mean the body skin. Hereinbelow, for convenience of the description, the specification is mainly described for the case where a target is the body skin, but the scope and spirit of the specification is not limited thereto.

A degree of penetration of the composition with respect to the body skin may be influenced by the skin temperature. Specifically, when the skin temperature is lowered at a predetermined level, skin cells shrink and a gap between the skin cells increases, and the composition penetrates through the gap between the skin cells, and as a result, the penetration of the composition can be improved.

Meanwhile, when the refrigerant and the composition are mixed and sprayed, various problems may occur. For example, the condensation of the composition may cause a problem in which the composition is not evenly sprayed, a problem in which the composition is not evenly distributed in a spray region of the refrigerant, and a problem of freezing of the composition due to the refrigerant.

At this point, the problem in which the composition is not evenly sprayed due to the condensation of the composition or the problem in which the composition is not evenly distributed in the spray region of the refrigerant may result the penetration degradation.

Specifically, in order to allow the composition penetration to be effective, the composition needs to be sprayed with a sufficiently strong force (or pressure). When the size of the composition increases (or the mass thereof increases) while the composition colliding with the sprayed refrigerant (or receiving kinetic energy of the sprayed refrigerant), according to law of conservation of momentum, the spraying speed of the composition may be reduced. In other words, the total amount of energy possessed by the sprayed refrigerant is divided and shared by the composition, and at this point, as the composition is divided into more even size of particles, the composition can be sprayed with a stronger force (or faster speed), and therefore, the penetration force can be improved.

Furthermore, the problem of freezing the composition by the refrigerant may serve to cause the mixture spray system or the mixing module not to be operated, or to cause the inconvenience to a person receiving treatment.

In the specification, the mixing module improved in penetration and convenience by removing the above-described problems will be described.

1. The Mixture Spray System

Hereinbelow, before the mixing module is described, the mixture spray system and an aspect of using the mixing module in the mixture spray system will be described first with reference to FIGS. 1 and 2.

FIG. 1 is a view showing a mixture spray system 100 according to an embodiment.

Referring to FIG. 1, the mixture spray system 100 may include a mixing module 1000 and a refrigerant providing device 2000.

First, the refrigerant providing device 2000 may mean a device that supplies a refrigerant. Specifically, the refrigerant providing device 2000 may supply the refrigerant to the mixing module 1000. The refrigerant providing device 2000 may be called by various names such as a refrigerant spray device, a spray device, or the like.

The refrigerant providing device 2000 may be configured to store the refrigerant therein, or to be supplied with the refrigerant from a separate refrigerant storage means. For example, as described below, the refrigerant providing device 2000 is coupled to a cartridge storing the refrigerant therein, and may obtain the refrigerant from the cartridge coupled thereto. As another example, the refrigerant providing device 2000 may be supplied with the refrigerant from an external refrigerant reservoir through a hose.

The refrigerant providing device 2000 may determine the characteristic of the supplied refrigerant. For example, the refrigerant providing device 2000 may control a supply amount, a supply time, temperature and/or pressure, etc. of the refrigerant.

The mixing module 1000 may be supplied with the refrigerant from the refrigerant providing device 2000.

The mixing module 1000 may store the composition therein. For example, the mixing module 1000 may include a container storing the composition therein as described below. Otherwise, the mixing module 1000 may be supplied with the composition from an external part.

The mixing module 1000 may supply a mixing space in which the refrigerant and the composition are mixed together. A method for mixing the refrigerant and the composition will be described below.

Figure 2:
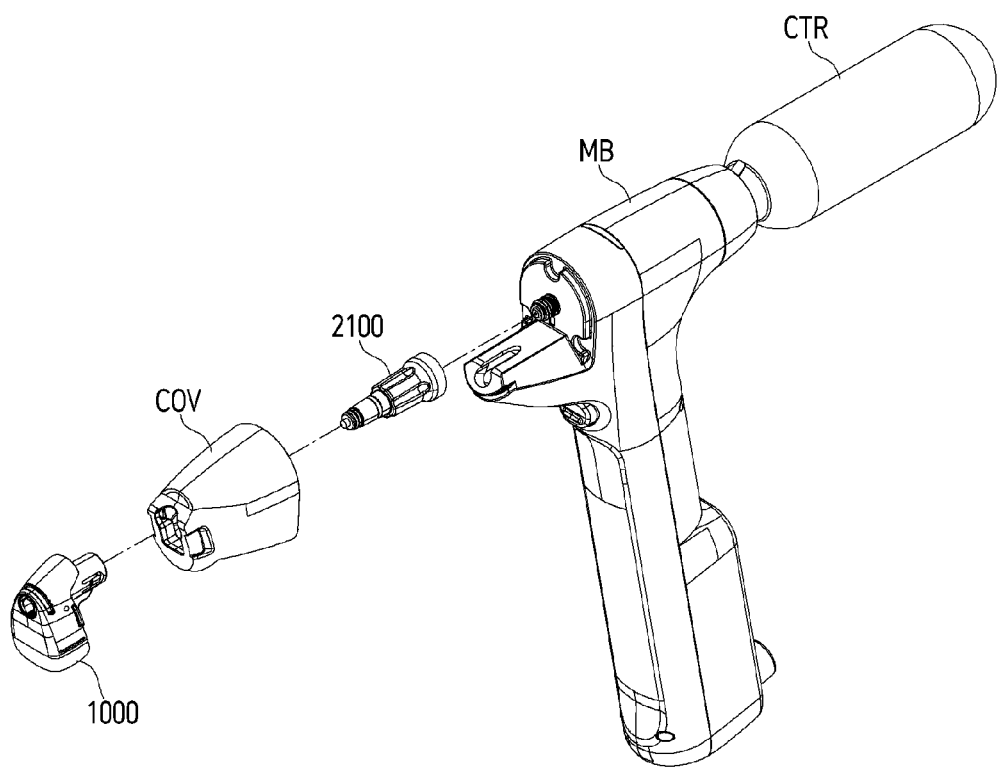
FIG. 2 is a view showing a process in which components of the mixture spray system are coupled to each other according to one embodiment.

FIG. 2 is a view showing a process in which components of the mixture spray system 100 are coupled to each other according to one embodiment.

The mixing module 1000 may be detached from or attached to the refrigerant providing device 2000. Specifically, the mixing module 1000 may be mounted to or separated from one component of the refrigerant providing device 2000.

Referring to FIG. 2, the refrigerant providing device 2000 may include a main body MB, a refrigerant spray unit 2100 coupled to the main body MB, and a cartridge CTR, and the mixing module 1000 may be coupled to the refrigerant spray unit 2100.

Moreover, the mixture spray system 100 may further include a cover COV that covers the refrigerant spray unit 2100. The cover COV may be coupled to the main body MB of the refrigerant providing device 2000.

Referring to FIG. 2, the refrigerant spray unit 2100 and the cover COV may be successively coupled to the main body MB, and then the mixing module 1000 may be coupled to the refrigerant spray unit 2100. The cover COV may form a space for the refrigerant spray unit 2100 to pass therethrough. Accordingly, when the cover COV is coupled to the main body MB, the refrigerant spray unit 2100 may penetrate through the cover COV.

The cover COV may be omitted in the mixture spray system 100. Otherwise, in the mixture spray system 100, the cover COV may be implemented as a part of the mixing module 1000. Otherwise, in the mixture spray system 100, the cover COV may be implemented as a part of the refrigerant providing device 2000.

Hereinabove, the case in which the mixture spray system 100 is divided into a plurality of components and the divided components are coupled to and separated from each other has been described. As described above, as the mixing module 1000 is separable from the refrigerant providing device 2000, the mixing module 1000 can be used disposable. Otherwise, the mixing module 1000 that has been used once or more may be washed and reused.

Meanwhile, the refrigerant spray unit 2100 and the mixing module 1000 of the mixture spray system 100 may be implemented as an integral body in which the refrigerant spray unit 2100 and the mixing module 1000 are connected to each other physically. Moreover, the mixing module 1000 and the refrigerant providing device 2000 in the mixture spray system 100 may be implemented as an integral body in which the mixing module 1000 and the refrigerant providing device 2000 are connected to each other physically. For example, the refrigerant spray unit 2100 may be comprised as a part of the mixing module 1000. As another example, the refrigerant spray unit 2100 and the mixing module 1000 may be comprised as a part of the refrigerant providing device 2000.

2. The Refrigerant Providing Device

Hereinbelow, the refrigerant providing device 2000 will be described with reference to FIG. 3.

Figure 3:
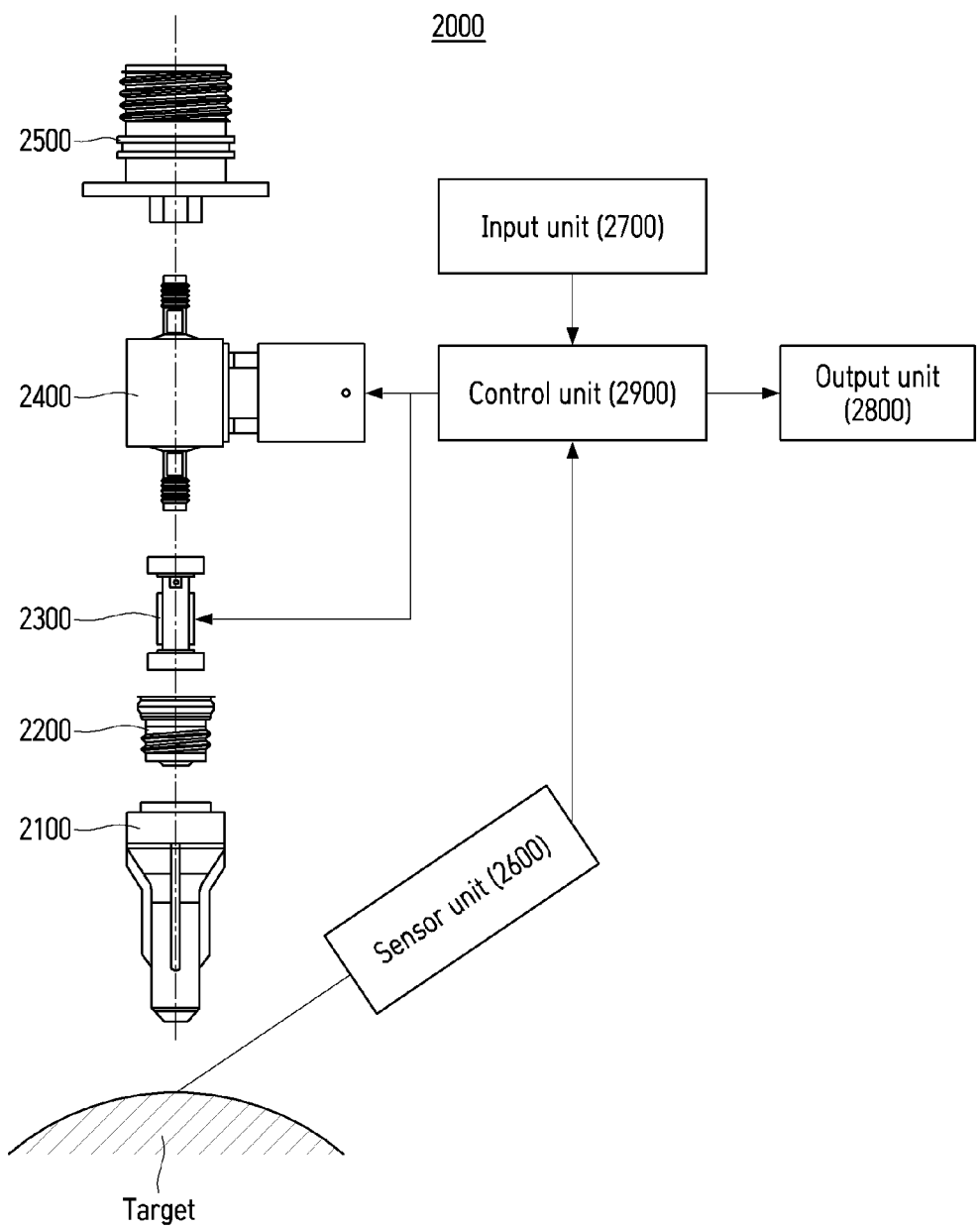
FIG. 3 is a view showing the components of a refrigerant providing device according to one embodiment.

FIG. 3 is a view showing the components of the refrigerant providing device 2000 according to one embodiment.

Referring to FIG. 3, the refrigerant providing device 2000 may include the refrigerant spray unit 2100, a spray part coupling unit 2200, a temperature adjustment unit 2300, a flow rate adjustment unit 2400, a cartridge coupling unit 2500, a sensor unit 2600, an input unit 2700, an output unit 2800, and a control unit 2900.

The refrigerant spray unit 2100 may include a structure to spray the refrigerant. Specifically, the refrigerant spray unit 2100 may form a flow path extending from one end to the other end, and may include a portion having a relatively narrower width of the flow path. A fluid passing through the refrigerant spray unit 2100 passes through the narrow portion of the flow path to be lowered in pressure to expand, and as a result, the fluid may be sprayed with a high speed. At this point, adiabatic expansion of the fluid is achieved while the fluid passes through the refrigerant spray unit 2100 so that the fluid has a low temperature, and the temperature of the refrigerant may be control to a temperature suitable for the procedure or treatment by the temperature adjustment unit 2300 to be described below.

The refrigerant spray unit 2100 may be understood as a nozzle. However, the technical idea of the specification is not limited thereto and the refrigerant spray unit 2100 may be understood as a component including a flow moving path having an arbitrary tubular shape.

The refrigerant spray unit 2100 may be attached to and detached from the main body MB of the refrigerant providing device 2000. For example, the refrigerant spray unit 2100 may be coupled to or separated from the main body MB through the spray part coupling unit 2200. Otherwise, the refrigerant spray unit 2100 may be physically connected to the main body MB of the refrigerant providing device 2000 to be integrally formed with the main body MB.

As described above, the mixing module 1000 may be coupled to the refrigerant spray unit 2100. To this end, the refrigerant spray unit 2100 and the mixing module 1000 may respectively include coupling parts or coupling members.

Meanwhile, the mixing module 1000 may be designed into various shapes as described below. Specifically, the mixing module 1000 may vary in a structure thereof according to the type of the composition to be used. As a result, according to the type of the mixing module 1000 coupled to the refrigerant spray unit 2100, a function or an effect to be generated using the mixture spray system 100 may be different.

The spray part coupling unit 2200 may be coupled to the refrigerant spray unit 2100. Meanwhile, when the refrigerant spray unit 2100 is omitted from the mixture spray system 100 or when the refrigerant spray unit 2100 becomes a part of the mixing module 1000, the mixing module 1000 may be coupled to the spray part coupling unit 2200.

A flow path through which the refrigerant is moved may be formed in the spray part coupling unit 2200. For example, the spray part coupling unit 2200 may include an outlet hole, and the refrigerant may be moved to the refrigerant spray unit 2100 coupled to the spray part coupling unit 2200, through the outlet hole.

The temperature adjustment unit 2300 may adjust the temperature of the refrigerant. For example, the temperature adjustment unit 2300 may supply thermal energy to the refrigerant so that the temperature of the refrigerant may increase, and according to the amount of the thermal energy supplied from the temperature adjustment unit 2300, the temperature of the refrigerant may be adjusted. The refrigerant sprayed through the refrigerant spray unit 2100 may have a relatively low temperature as described above, and at this point, the temperature of the refrigerant may be different according to the thermal energy supplied from the temperature adjustment unit 2300.

The temperature adjustment unit 2300 may include a heat generator generating thermal energy and a heat transmitter transmitting the generated thermal energy to the flow path in which the refrigerant is moved. For example, the heat generator may include an element using the thermoelectric effect, such as the Peltier effect and may generate thermal energy in response to electricity applied and the heat generator.

The flow rate adjustment unit 2400 may control movement of the refrigerant. For example, the flow rate adjustment unit 2400 may include a valve, and may open and close the valve by receiving a signal from the control unit 2900. Depending on whether the valve is opened or closed, the refrigerant may be moved or may not be moved. Depending on the opening and closing degree of the valve, the flow degree of the refrigerant may be controlled.

The cartridge coupling unit 2500 may accommodate at least a part of the above-described cartridge CTR. At this point, the cartridge CTR may be understood as a container storing the refrigerant therein. Specifically, the cartridge CTR may store the refrigerant therein under a predetermined pressure, and the predetermined pressure may be determined between approximately 35 bar to 100 bar based on 0~40° C. The pressure in the cartridge CTR may affect the spray amount or the spray shape of the refrigerant, and may indirectly affect the spray amount of the composition.

While the cartridge CTR is coupled to the cartridge coupling unit 2500, the refrigerant stored in the cartridge CTR may be moved to the main body MB.

The sensor unit 2600 may measure the temperature of a portion where the refrigerant is sprayed. For example, the sensor unit 2600 may measure the temperature of the skin surface to which the refrigerant is sprayed and may provide the measurement information to the control unit 2900.

The input unit 2700 may receive an input of a user. For example, the input unit 2700 may include at least one push button switch, and a push input signal may be provided to the control unit 2900 according to a pressure applied to the switch by the user, and the control unit 2900 may control opening and closing of the flow rate adjustment unit 2400 on the basis of the push input signal. Furthermore, the input unit 2700 may include at least one rotary switch, and may provide a rotary input signal to the control unit 2900 depending on operation of the user, and the control unit 2900 may preset target cooling temperature or target cooling time on the basis of the rotary input signal. At this point, the target cooling temperature may mean a temperature at which a target to which the user wants to cool. Here, the target is a site to be sprayed with a refrigerant (for example, a skin surface). In addition, the target cooling time may mean the time for which spray of the refrigerant should be maintained or the time for which the temperature of the skin surface should remain at the target cooling temperature.

The output unit 2800 may output interface and a variety of information for the user to use the refrigerant providing device 2000. For example, the output unit 2800 may include a display, and may output the interface for setting the target cooling temperature, the target cooling time, etc., through the display, and during operation of the refrigerant providing device 2000, the output unit 2800 may output the real time temperature of the skin surface measured by the sensor unit 2600 or the total time when the refrigerant is sprayed.

The control unit 2900 may control the components of the refrigerant providing device 2000. For example, the control unit 2900 may control the temperature adjustment unit 2300 to control the temperature of the refrigerant, and may control the flow rate adjustment unit 2400 to control a flow of the refrigerant, and may output specific information for the user through the output unit 2800.

Referring to FIG. 3, the refrigerant providing device 2000 may be operated as follows.

The control unit 2900 may first preset the target cooling temperature and/or the target cooling time. The control unit 2900 may provide the interface that induce the user to preset the target cooling temperature and/or the target cooling time, through the output unit 2800, and the control unit 2900 may receive a setting input signal according to the operation of the user through the input unit 2700, and may preset the target cooling temperature and/or the target cooling time on the basis of the received setting input signal.

Then, the control unit 2900 may output a message indicating that operation preparing is completed, to the user through the output unit 2800, and the control unit 2900 may receive a switch-on input signal according to operation of the user through the input unit 2700, and may spray the refrigerant on the basis of the received switch-on input signal.

While spraying the refrigerant, the control unit 2900 may obtain a temperature value that the temperature of the target to which the refrigerant is sprayed is measured, by the sensor unit 2600, and may control the temperature adjustment unit 2300 by comparing the obtained temperature value and the preset target cooling temperature. At this point, when the obtained temperature value is lower than the target cooling temperature, the control unit 2900 increases thermal energy applied to the refrigerant by the temperature adjustment unit 2300, and when the obtained temperature value is higher than the target cooling temperature, the control unit 2900 may decrease thermal energy applied to the refrigerant by the temperature adjustment unit 2300.

The refrigerant providing device 2000 is not limited to the above-described embodiment, and any device and structure performing the function of supplying the refrigerant may be understood as the refrigerant providing device 2000 described in the specification.

As an example, the refrigerant providing device 2000 may control the temperature of the refrigerant in a shape of continuously supplying a predetermined amount of thermal energy to the refrigerant without monitoring the temperature of the target. In this case, the step of presetting or receiving the target cooling temperature may be omitted.

3. The Mixing Module

Hereinbelow, the mixing module 1000 will be generally described with reference to FIGS. 4 to 6.

Figure 4:
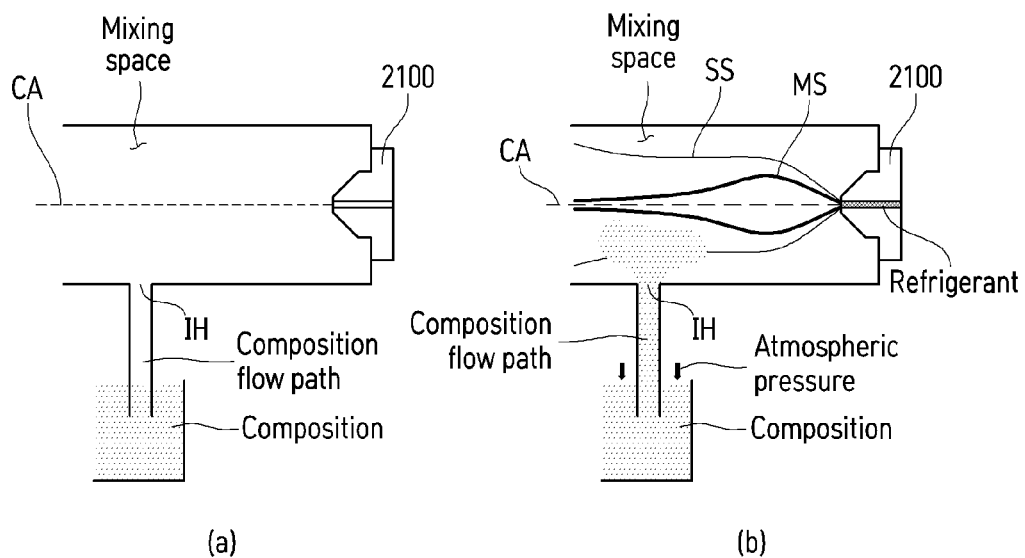
FIG. 4 is a view showing mixing principle of a refrigerant and a composition according to one embodiment.

FIG. 4 is a view showing mixing principle of a refrigerant and a composition according to one embodiment.

First, as shown in FIG. 4(*a*), it may be considered that the tubular mixing space includes the refrigerant spray unit 2100 to spray the refrigerant and an inlet hole IH to introduce the composition.

The container storing the composition therein and the inlet hole IH may be fluidly connected to each other through the composition flow path. The composition flow path may be formed in a direction perpendicular to a center axis CA of the refrigerant spray unit 2100, but is not limited thereto.

Referring to FIG. 4(*b*), when the refrigerant is sprayed from the refrigerant spray unit 2100, spraying shape of the refrigerant may be divided into a main stream MS and a sub stream SS on the basis of the center axis of the refrigerant spray unit 2100.

The main stream MS may mean a region where the refrigerant is sprayed relatively strong and the sub stream SS may mean a region where the refrigerant is sprayed relatively light.

Furthermore, the main stream MS may be formed within a predetermined distance based on the center axis CA of the refrigerant spray unit 2100, and the sub stream SS may be formed out of a predetermined distance based on the center axis CA of the refrigerant spray unit 2100. However, a standard of dividing the main stream MS and the sub stream SS is not limited to the above-described standard.

As described below, by a negative pressure generated while spraying the refrigerant, the composition may be introduced into the main stream MS or the sub stream SS of the refrigerant and mixed with the refrigerant, and the mixed refrigerant and composition may be sprayed together. However, the force applied by the refrigerant to the composition in the main stream MS and the sub stream SS may be different.

The refrigerant sprayed from the refrigerant spray unit 2100 may pass near the inlet hole IH. When the refrigerant at relatively faster speed passes near the inlet hole IH, negative pressure may be formed near the inlet hole IH according to Bernoulli's equation. The composition may be introduced into the mixing space through the inlet hole by the negative pressure formed near the inlet hole IH and mixed with the refrigerant. Specifically, an external force equal to atmospheric pressure may be continuously applied into the container in which the composition is stored, and it may be understood that the composition moves as the external force becomes greater than the negative pressure.

The composition introduced into the inlet hole IH may collide with the refrigerant during a process of mixing the composition and the refrigerant, and accordingly, the composition may be divided into fine particles to be sprayed.

Figure 5:
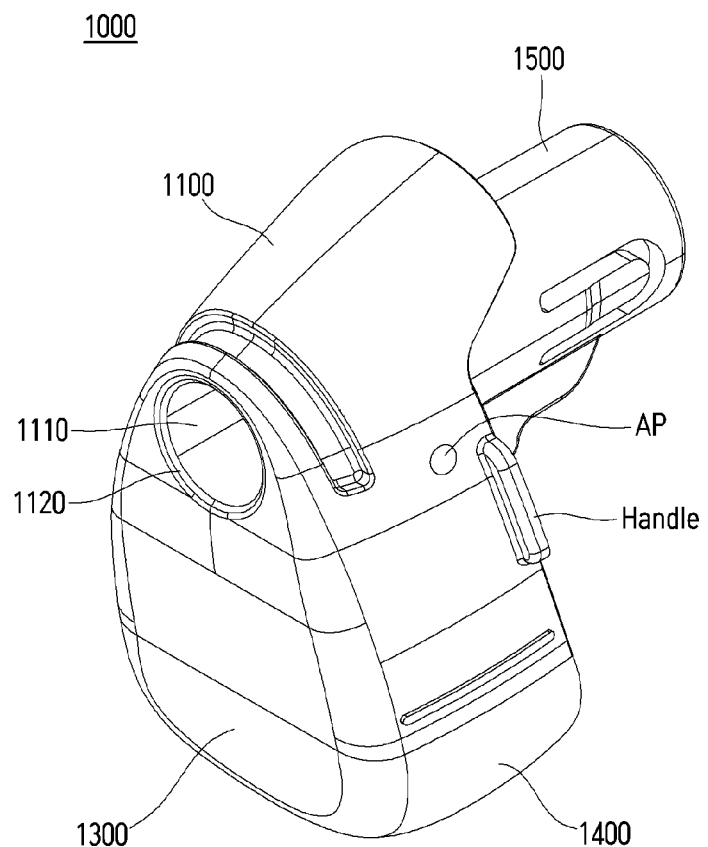
FIG. 5 is a view showing a mixing module according to one embodiment.

FIG. 5 is a view showing the mixing module 1000 according to one embodiment.

Figure 6:
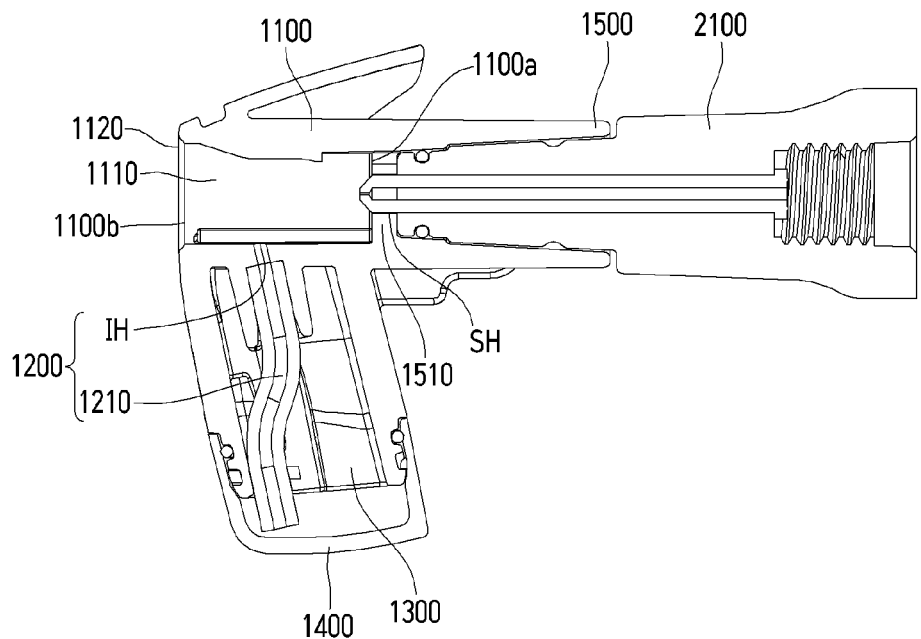
FIG. 6 is a sectional view showing a state in which the mixing module is coupled to a refrigerant spray unit according to one embodiment.

FIG. 6 is a sectional view showing a state in which the mixing module 1000 is coupled to the refrigerant spray unit 2100 according to one embodiment.

Referring to FIGS. 5 and 6, the mixing module 1000 may include a mixing part 1100, a composition inflow part 1200, a composition storing part 1300, a cap 1400, and a fastening part 1500.

The mixing part 1100 may provide a mixing space 1110 where the refrigerant and the composition are mixed together. Specifically, an inner surface of the mixing part 1100 may define the mixing space 1110, and the inlet hole IH and an insertion hole SH may be formed on the inner surface of the mixing part 1100. Meanwhile, when the refrigerant spray unit 2100 is provided as a part of the mixing module 1000 or may be omitted, the insertion hole SH may be omitted.

The mixing part 1100 may include a mixture spraying hole 1120. The mixture spraying hole 1120 may be understood as a boundary where the refrigerant and the composition are sprayed out of the mixing module 1000.

The composition inflow part 1200 may mean a part into which the composition is introduced. Specifically, the composition inflow part 1200 may serve to fluidly connect the composition storing part 1300 storing the composition therein and the mixing space of the mixing part 1100. To this end, the composition inflow part 1200 may form a tube 1210 to move the composition and the inlet hole IH described above.

The tube 1210 may provide a flow path through which the composition is moved. The tube 1210 may fluidly connect the composition storing part 1300 and the mixing part 1100.

The tube 1210 may have various shapes. For example, referring to FIG. 6, the tube 1210 may be implemented in a form including a bent part. More specifically, the tube 1210 may have a form that is bent in a distal direction. At this point, the distal direction may be understood as a direction in which the refrigerant is sprayed or a direction directing from a first end **1100*a* to a second end 1100*b* of the mixing part 1100. Otherwise, one end of the tube 1210 located in the composition storing part 1300 may be located in a portion separated in the above-described distal direction on the basis of a center axis of the composition storing part 1300. The form of the tube 1210 causes the effect that the composition stored in the composition storing part 1300 is used as much as possible, when considering the aspect of use of the mixture spray system 100. For example, when the mixture spray system 100 shown in FIG. 2 is used to spray the refrigerant and the composition, spraying direction generally directs from the upper side (direction opposite to gravity) to the lower side (direction of gravity), and in this case, the composition in the composition storing part 1300 may be moved in the distal direction (or forwards) due to gravity. Therefore, in order to use the composition in the composition storing part 1300 as much as possible, one end of the tube 1210 needs to be located in a location to which the composition is moved, i.e., a front space based on the center axis of the composition storing part 1300**.

The inlet hole IH may be formed in the inner surface of the mixing part 1100. The inlet hole IH may have a section in parallel to the center axis of the mixing part 1100 on the inner surface of the mixing part 1100.

The tube 1210 and the inlet hole IH may be understood as an integral body. For example, a part of the tube 1210 may be understood as the inlet hole IH. For example, one end of the tube 1210 may be understood as the inlet hole IH.

Otherwise, the tube 1210 and the inlet hole IH may be provided as separate components, and the tube 1210 may be implemented in a form coupled to the inlet hole IH.

Meanwhile, the direction in which the composition flows into the mixing part 1100 may be determined according to the position of the inlet hole IH. For example, as shown in FIG. 6, when the inlet hole IH is located at the lower part of the inner side of the mixing part 1100, inflow direction of the composition may be closer to the opposite direction of gravity than the direction of gravity. For another example, when the inlet hole IH is located at upper part of the inner side of the mixing part 1100, inflow direction of the composition may be closer to the direction of gravity than the opposite direction of gravity. Hereinafter, a case in which the inlet hole IH is located in the lower part of the inner side of the mixing part 1100 will be described, but the technical idea of the present disclosure is not limited thereto. Even when the inlet hole IH is located in the upper part of the inner side of the mixing part 1100, the following description may be applied likewise.

The composition storing part 1300 may provide a space receiving the composition. The composition storing part 1300 may provide a space storing the composition supplied from the outside space.

The composition stored in the composition storing part 1300 may be moved to the mixing part 1100 through the composition inflow part 1200.

Meanwhile, the composition may be continuously supplied from the outside space to the mixture spray system 100, and the composition storing part 1300 may be understood as a component providing a space for the composition continuously supplied to stay before being introduced into the mixing part 1100.

The cap 1400 may be a component sealing the composition storing part 1300. At this point, the composition may be stored in the composition storing part 1300 in the following method. The user can open the cap 1400 coupled to the composition storing part 1300 and put the composition contained in a separate composition container (e.g., ampule, cosmetics container, etc.) into the composition storing part 1300 and then close the cap 1400.

The fastening part 1500 may be fastened to the refrigerant spray unit 2100. The fastening part 1500 may include a support 1510 and the insertion hole SH. The refrigerant spray unit 2100 may be inserted into the insertion hole SH. The support 1510 may support the refrigerant spray unit 2100 inserted in the insertion hole SH. The fastening part 1500 and the refrigerant spray unit 2100 may respectively include members to be fastened to each other. A process in which the fastening part 1500 and the refrigerant spray unit 2100 are fastened to each other will be described below.

Referring to FIG. 5, the mixing module 1000 may include an external air passage AP and a handle.

The external air passage AP may be fluidly connected to the composition storing part 1300. The external air passage AP may allow the pressure in the composition storing part 1300 to be maintained in atmospheric pressure. Therefore, when negative pressure is generated in the inlet hole IH, pressure in the composition storing part 1300 more increases, so that the composition may be moved to the mixing part 1100 through the composition inflow part 1200.

The handle may be a component that may easily separate the mixing module 1000 from the refrigerant providing device 2000.

The above-described components of the mixing module 1000 may be independently manufactured and assembled to each other.

Otherwise, at least a part of the above-described components of the mixing module 1000 may be integrally formed. For example, the mixing part 1100, the composition storing part 1300, and the fastening part 1500 may be manufactured into an integral body physically connected to each other and the tube 1210 and the cap 1400 that may be manufactured separately may be assembled thereto. As another example, the mixing part 1100, the composition storing part 1300, and the tube 1210 may be manufactured into an integral body physically connected to each other, and the cap 1400 may be manufactured as a separate object and may be assembled thereto.

Meanwhile, the mixing module 1000 may be implemented differently from the above description. For example, the mixing module 1000 may include the above-described components and may include a container mounting part instead of the composition storing part 1300. The container mounting part is configured such that the composition container is coupled thereto, and may have a structure including a needle that may perforate a stopper of the composition container or other structures to which the composition container may be coupled. The container mounting part may be fluidly connected to the tube 1210 or the inlet hole IH.

In this case, the user can use the mixture spray system 100 in a form in which the composition container itself is coupled to the mixing module 1000, instead of putting the composition into the composition storing part 1300 of the mixing module 1000.

Hereinbelow, for the convenience of description, the specification is mainly described for the case where the mixing module 1000 includes the mixing part 1100, the composition inflow part 1200, the composition storing part 1300, the cap 1400, and the fastening part 1500, and the composition is transferred from a separate composition container to the composition storing part 1300, but the technical idea of the specification is not limited thereto.

Meanwhile, when the above-described mixing module 1000 is used, various problems may occur according to properties (e.g., viscosity, cohesion, freezing point, adhesion, or the like) of the composition. Hereinbelow, various problems that may occur in the mixing module 1000 and solutions (e.g., direction of design of the mixing module 1000) will be described in detail.

4. The Mixing Module Design

Hereinbelow, referring to FIG. 7, basic considerations and possible problems in design of the mixing module 1000 will be described.

Figure 7:
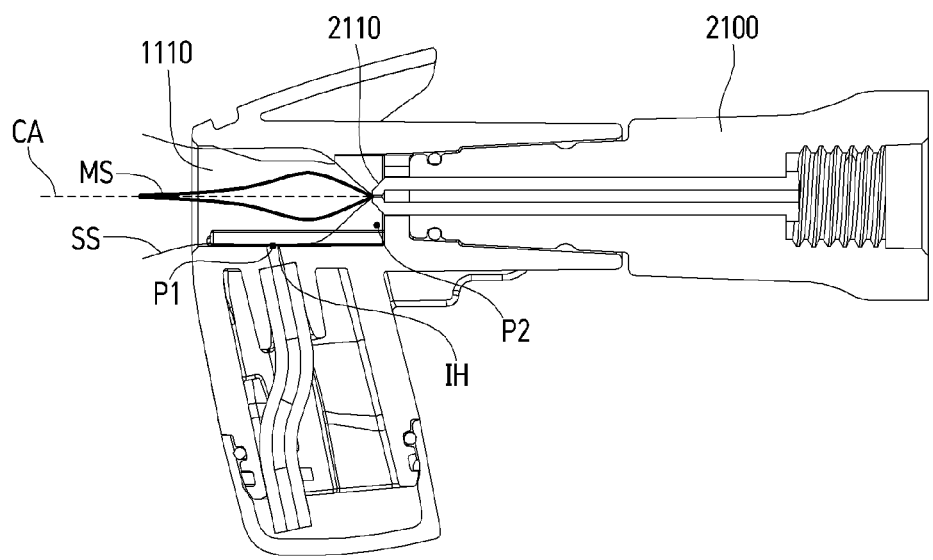
FIG. 7 is a view showing an aspect of spraying the refrigerant in the mixing module according to one embodiment.
Figure 8:
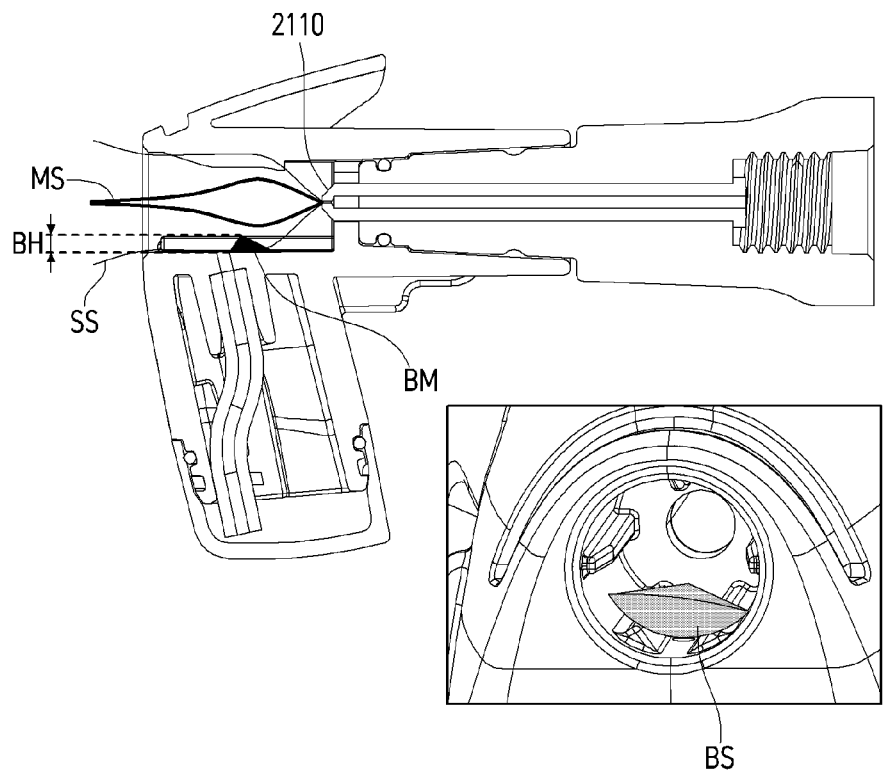
FIG. 8 is a view showing the mixing module including a block member according to one embodiment.
Figure 9:
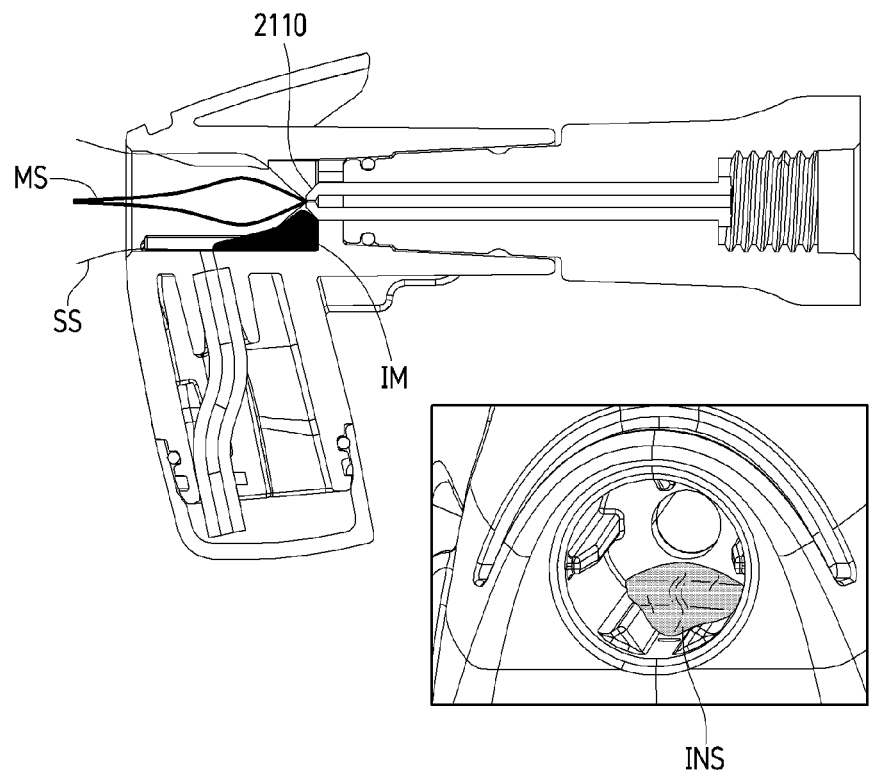
FIG. 9 is a view showing the mixing module including a filling member according to one embodiment.
Figure 10:
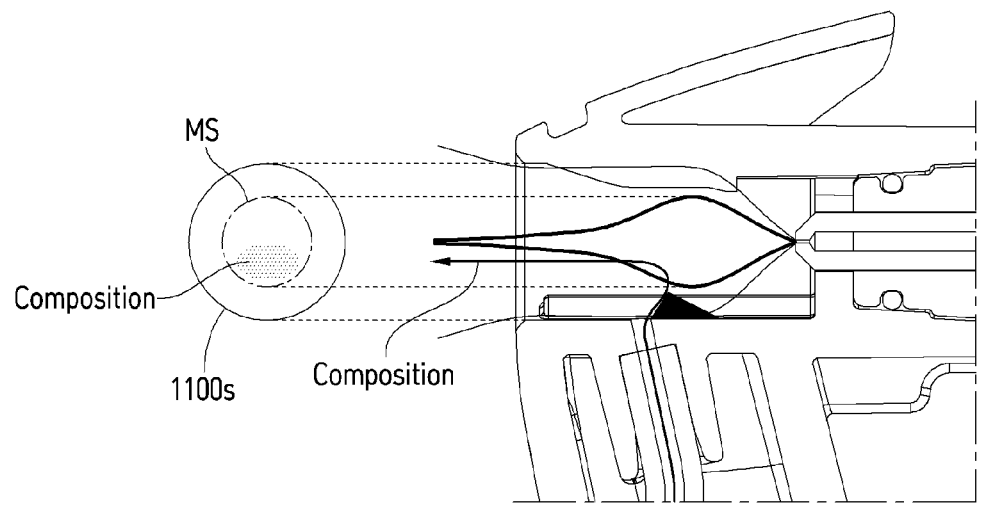
FIG. 10 is a view showing a process in which the composition is unevenly distributed in a refrigerant stream according to one embodiment.

FIG. 7 is a view showing an aspect of spraying the refrigerant in the mixing module 1000 according to one embodiment.

The mixing module 1000 is intended to move the composition by using refrigerant spray without a separate pressure device, and to this end, the mixing module uses negative pressure according to Bernoulli's equation described above.

Referring to FIG. 7, as the refrigerant is sprayed, spray stream of the refrigerant may be generated in the mixing part 1100 of the mixing module 1000. In order to move the composition from the composition storing part 1300 to the mixing space 1110, negative pressure should be generated in the inlet hole IH.

In order to generate negative pressure in the inlet hole IH, the spray stream may pass near the inlet hole IH. At this point, whether or not the spray stream passes near the inlet hole IH depends on the size of the spray stream, the width of the mixing part 1100, and the distance between a refrigerant spray hole 2110 and the inlet hole IH.

First, the size of the spray stream may mean the sectional size of the spray stream, and specifically, may mean the size of a section perpendicular to the center axis CA of the refrigerant spray unit 2100 in the sub stream SS. The sectional size of the spray steam may increase as being moved away from the refrigerant spray hole 2110. Furthermore, the sectional size of the spray stream may increase as spray angle in the refrigerant spray hole 2110 increases.

When the sectional size of the spray stream corresponds to the width of the mixing part 1100, a part of the spray stream may be understood as being close to or being in contact with the inner surface of the mixing part 1100. In other words, based on a direction of spraying the refrigerant, from a critical location moved away from the refrigerant spray hole 2110 by a predetermined distance, the spray stream may be close to the inner surface of the mixing part 1100 or may be in contact with the inner surface thereof.

In order to generate a negative pressure by the spray stream on the inlet hole IH formed on the inner surface of the mixing part 1100, a location of the inlet hole IH should be determined based on the above-described critical location. For example, the inlet hole IH may be formed in the critical location. As another example, the inlet hole IH may be formed within a predetermined distance in the distal direction (spraying direction of refrigerant) based on the critical location. As another example, the inlet hole IH may be formed within a predetermined distance in a proximal direction (direction opposite to spraying direction of refrigerant) based on the critical location.

Meanwhile, the size of the spray stream is relatively small near the refrigerant spray hole 2110, in comparison to the width of the mixing part 1100, so that the spray stream may not be generated in the inner surface of the mixing part 1100. Therefore, the inlet hole IH needs to be formed to be spaced apart from the refrigerant spray hole 2110 by a predetermined distance in the distal direction (spraying direction of refrigerant).

4.1. Possible Problem #1 and Solution Plan

Meanwhile, as described above, the spray stream may be divided into the main stream MS and the sub stream SS, and the spray speed of the refrigerant may be different in the main stream MS and the sub stream SS. Specifically, the moving speed of the refrigerant in the main stream MS may be larger than the moving speed of the refrigerant in the sub stream SS.

Due to a difference in the moving speed of the refrigerant for each region, a pressure difference may exist between partial regions inside the mixing part 1100. For example, referring to FIG. 7, a relatively low air pressure may be generated around the refrigerant spray hole 2110 where the refrigerant is moved relatively fast in the mixing part 1100.

More specifically, when the refrigerant is sprayed, by Bernoulli's equation, a first air pressure may be generated at a first low pressure point P1 near the inlet hole IH, and a second air pressure may be generated at a second low pressure point P2 near the refrigerant spray hole 2110.

At this point, since the moving speed of the refrigerant near the inlet hole IH is faster than the moving speed of the refrigerant at the refrigerant spray hole 2110, the second air pressure at the second low pressure point P2 may be lower than the first air pressure at the first low pressure point P1. In other words, the composition introduced through the inlet hole IH may receive a force to move to the second low pressure point P2 where the second air pressure lower than the first air pressure is formed.

Meanwhile, a force of the spray stream applied to the composition introduced through the inlet hole IH may be different according to region. For example, a force of the refrigerant applied to the composition in the sub stream SS may be smaller than a force of the refrigerant applied to the composition in the main stream MS. Moreover, as a force affecting movement of the composition in the sub stream SS, an external force generated by a difference between the first air pressure and the second air pressure may be greater than a force by the refrigerant.

Accordingly, with this reason, in order to spray the composition introduced into the mixing part 1100 together with the refrigerant, it is preferable that the composition is moved to the main stream MS of the refrigerant. Furthermore, the composition not to be moved to the main stream MS may be moved in a direction opposite to the spraying direction of the refrigerant by an air pressure difference, or may be moved to the second air pressure point P2, rather than being sprayed by the sub stream SS.

The compositions moved near the second air pressure point P2 or the refrigerant spray hole 2110 may be condensed to each other according to properties thereof. The condensed composition may be sprayed by the refrigerant in a relatively large volume, and thus the compositions having different particle sizes may be sprayed from the mixing module 1000. This uneven composition spray results problems in that the penetration effect of the composition with respect to the target and moreover a recipient (or subject to be treated) feels discomfort.

In order to solve the above-described problems, a structure or a device is required to induce the composition to reach the main stream MS. Otherwise, a structure or a device may be used to prevent the composition from being moved to the second low pressure point P2.

Hereinbelow, a structure of the mixing module 1000 to solve the above-described problems will be described with reference to FIGS. 8 and 9.

FIG. 8 is a view showing the mixing module 1000 including a block member BM according to one embodiment.

Referring to FIG. 8, the block member BM may be formed in the inner surface of the mixing part 1100 of the mixing module 1000. The block member BM may prevent the composition from being moved to the refrigerant spray hole 2110 or the second end 1100*b* of the mixing part 1100.

The block member BM may include a block surface BS.

The block surface BS may be in contact with a part of the composition inflow part 1200. For example, the block surface BS may be in contact with the inlet hole IH or may extend from the inlet hole IH.

The composition introduced through the inlet hole IH may be moved over the block surface BS of the block member BM to reach the main stream MS of the refrigerant. Accordingly, the composition may not be moved to the second low pressure point P2 near the refrigerant spray hole 2110.

The block surface BS may have a preset block angle with respect to the inlet hole IH. For example, the block surface BS may have a preset first angle with respect to an imaginary plane including a section of the inlet hole IH. At this point, the preset block angle may be determined between 0° to 90°. The block surface BS may be a plane, a curved surface, or a combination thereof.

The block member BM may have a preset block height BH. The block height BH may mean the height of the block member BM in a direction perpendicular to the center axis of the mixing part 1100 based on the inlet hole IH.

The block height BM may be preset as the height of the main stream MS of the refrigerant. For example, when the width of the main stream MS is half of the width of the mixing part 1100, the block height may be determined below half of the width of the mixing part 1100.

The block member BM may be integrally formed with the mixing part 1100. Specifically, the block member BM may be shaped to protrude from the inner surface of the mixing part 1100.

The block member BM may be coupled to the inner surface of the mixing part 1100 while being formed separately from the mixing part 1100.

Meanwhile, when the block member BM is used to block condensation of the composition, the composition used for mix and spray needs to have relatively low adhesion. At this point, adhesion may be understood as a force of pulling between the block member BM and the composition. Therefore, when the composition having high adhesion is used, the composition rises over the block surface BS of the block member BM and as a result, the effect in which the composition is condensed in the second low pressure point P2 may occur.

Furthermore, when the block member BM is used, the composition used for mix and spray needs to have a relatively high freezing point. This is because the temperature of the block member BM may be reduced by the sprayed refrigerant and therefore the temperature of the composition moved over the block member BM is also lowered to result a problem in that the composition is sprayed in a frozen state.

FIG. 9 is a view showing the mixing module 1000 including an inclined member IM according to one embodiment.

A region where the composition is condensed in the mixing part 1100 of the mixing module 1000 may be filled. Referring to FIG. 9, the mixing module 1000 may include the inclined member IM.

The inclined member IM may be understood as a block having an inclination, a slope way, or a ramp. The inclined member IM may be disposed between the inlet hole IH and the refrigerant spray hole 2110.

The inclined member IM may include an inclined surface INS. The inclined surface INS may be implemented with a plane, a curved surface, or a combination thereof.

The inclined surface INS may be in contact with a part of the composition inflow part 1200. For example, the inclined surface INS may be in contact with the inlet hole IH or may extend from the inlet hole IH.

The inclined surface INS may extend from the composition inflow part 1200 to the vicinity of the refrigerant spray hole 2110. For example, the inclined surface INS may be in contact with the refrigerant spray hole 2110.

The inclined surface INS may be designed considering spray shape of the refrigerant. For example, the inclined surface INS may be designed to correspond to a shape of the main stream MS.

Otherwise, the inclined surface INS may be implemented in a form having inclination having a predetermined angle.

The inclined member IM may be integrally formed with the mixing part 1100. Specifically, the inclined member IM may be understood as a portion having an inclination in a part of the inner surface of the mixing part 1100.

The block member BM may be coupled to the inner surface of the mixing part 1100 while being produced separately from the mixing part 1100. Specifically, the inclined member IM may be disposed in the shape of an inclined block or an inclined plate on the inner surface of the mixing part 1100.

The composition introduced into the inlet hole IH may rise over the inclined surface INS of the inclined member IM, and may be sprayed by the main stream MS of the refrigerant during rising. As a result, the composition may be sprayed by the refrigerant before being condensed.

Meanwhile, when the inclined member IM is used, the composition used for spray needs to have a relatively high freezing point. This is because the temperature of the inclined member IM may be reduced by the sprayed refrigerant and therefore the temperature of the composition moved over the inclined member IM is also lowered to result a problem in that the frozen composition is sprayed.

4.2. Possible Problem #2 and Solution Plan

As described above, when the mixing module 1000 is designed such that the composition reaches the main stream MS of the refrigerant, condensation of the composition may be prevented, but a phenomenon in which the composition is not evenly mixed with the refrigerant may occur.

Specifically, when the block member BM is used in the mixing module 1000 as shown in FIG. 10, as shown in a mixing part section 1100*s* perpendicular to the center axis of the mixing part 1100, the composition may be sprayed to lean to a part (e.g., lower part) of the main stream MS of the refrigerant.

If the purpose is to evenly disperse and spray the composition throughout the main stream MS rather than spraying the composition more intensively in one area, it is necessary to prevent the above phenomenon from occurring.

In order to solve the above-described problem, the composition needs to be induced to be moved to an upper portion of the main stream MS of the refrigerant beyond reaching a lower portion of the main stream MS.

To this end, the mixing module 1000 may include the guide member. The guide member provides a surface on which the composition moves over, and the surface may be shaped for the composition to be moved to the upper portion of the main stream MS.

Specifically, the guide member may be implemented in a form that surrounds at least a part of the refrigerant. For example, the guide member may be implemented in a form that surrounds at least a part of the main stream MS. In this case, the guide member may avoid disturbing spray of the refrigerant and may allow the composition to spread to the upper portion of the main stream MS.

Hereinbelow, various embodiments of the guide member will be described with reference to FIGS. 11 to 19. Meanwhile, it is disclosed in advance that the guide member may be variously called by a guide plate, a spreading film, a metal film, a spreading plate, a heat exchange inducement member, a heat transfer member, an insert, etc., according to a form or a function thereof.

FIG. 11 is a view showing a guide plate 1610 according to one embodiment.

FIG. 12 is a view showing a process in which the composition is moved through the guide plate 1610 according to one embodiment.

FIG. 13 is a view showing a form of the guide plate 1610 based on the mixing part 1100 and a first plate 1611 of the guide plate 1610 according to one embodiment.

The guide plate 1610 may be disposed in the mixing part 1100 of the mixing module 1000 to guide movement of the composition. Hereinbelow, it is described that the guide plate 1610 is produced separately from the mixing part 1100 and is coupled to the mixing part 1100. However, the technical idea of the specification is not limited to the above description and the guide plate 1610 may be implemented in a state physically integrated with the mixing part 1100.

The guide plate 1610 may be understood as a structure composed of a plurality of surfaces. For example, referring to FIG. 11, the guide plate 1610 may include the first plate 1611 and a second plate 1612. At this point, the expression of the first and the second plate 1611, 1612 is a term used to refer to a component of the guide plate 1610, and may be expressed as a first and a second part, a first and a second frame, a first and a second structure, or the like.

The first plate 1611 may include at least a first plate surface S11 and a second plate surface S12.

At this point, the first plate surface S11 may mean a surface that is in contact with an inner surface of the mixing part 1100 when the first plate 1611 is disposed in the mixing part 1100. Specifically, the first plate 1611 is disposed close to the inlet hole IH as shown in FIG. 11, and at this point, the first plate surface S11 may be in contact with the inner surface of the mixing part 1100. The first plate surface S11 and the inner surface of the mixing part 1100 may be in planar-contact or linear-contact with each other.

The second plate surface S12 may mean a surface that is inclined at a preset angle with respect to the inlet hole IH when the first plate 1611 is disposed in the mixing part 1100. In other words, the second plate surface S12 may have a preset angle with respect to a flat surface including the inlet hole IH. At this point, the first plate surface S11 and the second plate surface S12 may have a specific angle therebetween. The composition introduced through the inlet hole IH may be moved over the second plate surface S12 by adhesion with the second plate surface S12.

The first plate surface S11 and the second plate surface S12 may be shaped in a flat surface, a curved surface, or a combination thereof.

The first plate surface S11 and the second plate surface S12 may be directly and indirectly connected to each other.

The first plate surface S11 and the second plate surface S12 may meet each other. In other words, the first plate surface S11 and the second plate surface S12 may be in contact with each other or may share one edge.

The first plate surface S11 and the second plate surface S12 may not meet each other, and in this case, an additional surface may be located between the first plate surface S11 and the second plate surface S12. At this point, a flat surface including the first plate surface S11 and a flat surface including the second plate surface S12 may meet each other or may be in parallel to each other.

The first plate 1611 may include an additional surface in addition to the first plate surface S11 and the second plate surface S12 described above.

The first plate 1611 may be implemented in various forms. As an example, the first plate 1611 may be implemented in a form that is bent or is folded at a predetermined angle as shown in FIG. 11. As another example, the first plate 1611 may be implemented in various forms such as a rectangular parallelepiped form, a form having a curved surface, and the like.

The second plate 1612 may include at least a third plate surface S13 and a fourth plate surface S14.

At this point, the third plate surface S13 may mean a surface that is in contact with the inner surface of the mixing part 1100 when the second plate 1612 is disposed in the mixing part 1100. Specifically, the second plate 1612 is disposed close to the inlet hole IH as shown in FIG. 11, and at this point, the third plate surface S13 may be in contact with the inner surface of the mixing part 1100. The third plate surface S13 and the inner surface of the mixing part 1100 may be in planar-contact or linear-contact with each other.

The fourth plate surface S14 may mean a surface that is inclined at a preset angle with respect to the inlet hole IH when the second plate 1612 is disposed in the mixing part 1100. In other words, the fourth plate surface S14 may have a preset angle with respect to a flat surface including the inlet hole IH. At this point, the third plate surface S13 and the fourth plate surface S14 may have a specific angle therebetween. The composition introduced through the inlet hole IH may be moved over the fourth plate surface S14 by adhesion with the fourth plate surface S14.

The third plate surface S13 and the fourth plate surface S14 may be shaped in a flat surface, a curved surface, or a combination thereof.

The third plate surface S13 and the fourth plate surface S14 may be directly and indirectly connected to each other.

The third plate surface S13 and the fourth plate surface S14 may meet each other. In other words, the third plate surface S13 and the fourth plate surface S14 may be in contact with each other or may share one edge.

The third plate surface S13 and the fourth plate surface S14 may not meet each other, and in this case, an additional surface may be provided between the third plate surface S13 and the fourth plate surface S14. At this point, a flat surface including the third plate surface S13 and a flat surface including the fourth plate surface S14 may meet each other or may be in parallel to each other.

The second plate 1612 may include an additional surface in addition to the third plate surface S13 and the fourth plate surface S14 described above.

Figure 11:
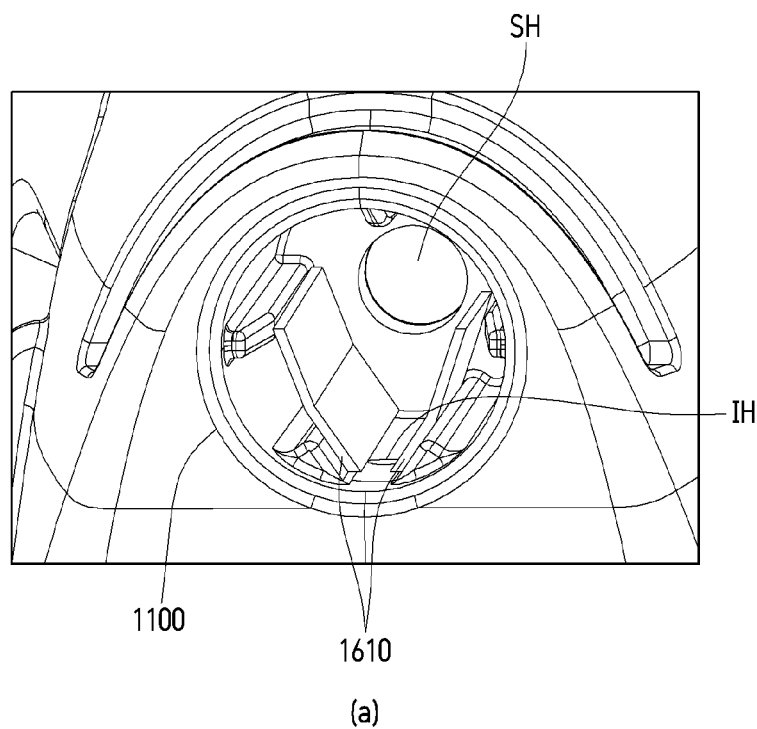
FIG. 11 is a view showing a guide plate according to one embodiment.
Figure 11:
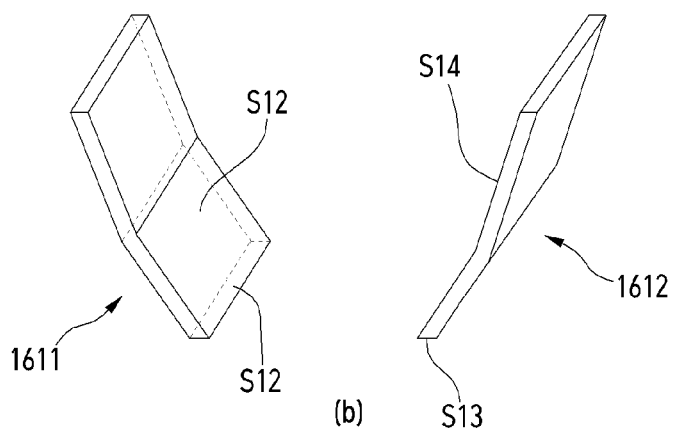

The second plate 1612 may be implemented in various forms. As an example, the second plate 1612 may be implemented in a form that is bent or is folded at a predetermined angle as shown in FIG. 11. As another example, the second plate 1612 may be implemented in various forms such as a rectangular parallelepiped form, a form having a curved surface, and the like.

Figure 12:
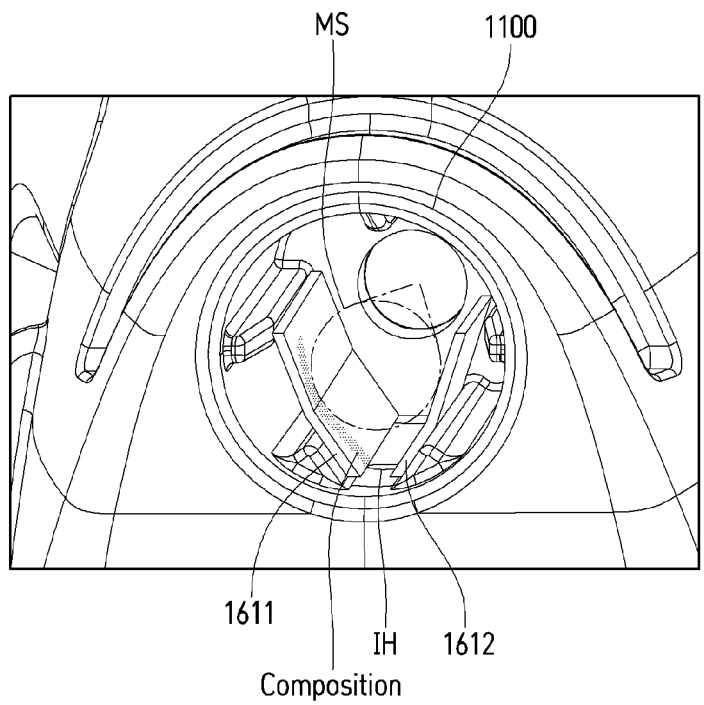
FIG. 12 is a view showing a process in which the composition is moved through the guide plate according to one embodiment.

The first plate 1611 and the second plate 1612 may be disposed to have a specific locational relationship in the mixing part 1100. As an example, referring to FIG. 11(a) or FIG. 12, the first plate 1611 and the second plate 1612 may be disposed to be spaced apart from each other. At this point, the inlet hole IH may be located between the first plate 1611 and the second plate 1612.

The first plate 1611 and the second plate 1612 may be disposed to be symmetric to each other in the mixing part 1100.

Meanwhile, the guide plate 1610 may include only one of the first plate 1611 and the second plate 1612.

Figure 13:
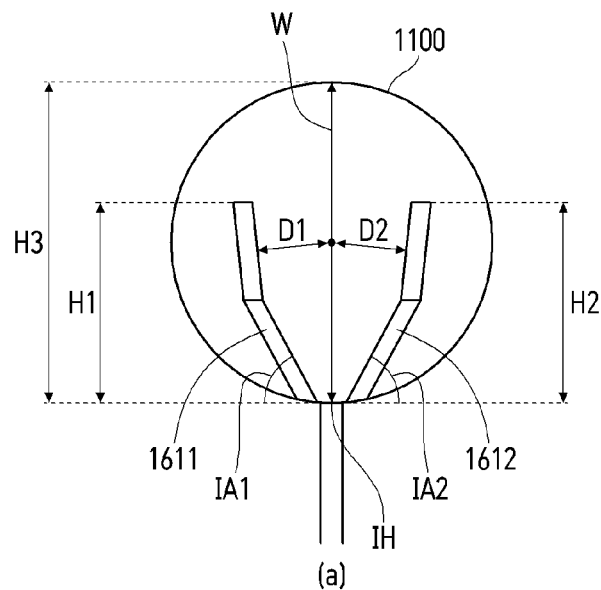
FIG. 13 is a sectional view showing a mixing part in which the guide plate is disposed and a view showing a first plate of the guide plate according to one embodiment.
Figure 13:
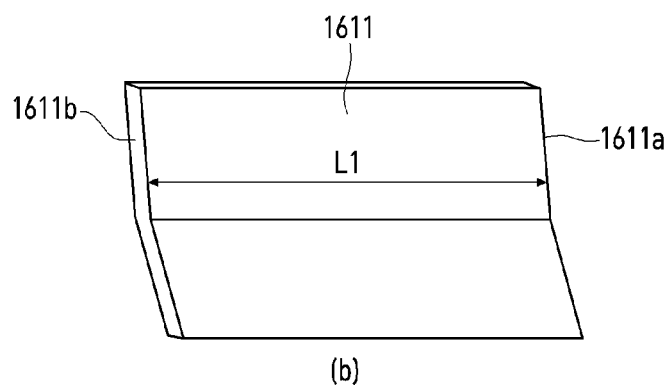

Referring to FIG. 13, the composition introduced through the inlet hole IH may be moved over the guide plate 1610. The composition moved over the guide plate 1610 may be mixed to the main stream MS of the refrigerant to be sprayed together. As described below, when the height of the guide plate 1610 is sufficiently high, the composition may reach the upper portion of the main stream MS. Accordingly, the composition is mixed with the refrigerant at not only the lower portion of the main stream MS but also the upper portion, and as a result, the composition may be evenly distributed throughout the main stream MS.

As described above, in order to allow the composition moved over the guide plate 1610 to reach the upper portion of the main stream MS, the guide plate 1610 needs to be designed to have a specific size.

Referring to FIG. 13(a), the guide plate 1610 may be designed to have a predetermined height, a predetermined distance, and a predetermined inclined angle.

A height of the guide plate 1610 may mean a height when the guide plate 1610 is disposed in the mixing part 1100. As an example, the first plate 1611 may have a first height H1 in a direction perpendicular to the center axis of the mixing part 1100 based on the inlet hole IH. The second plate 1612 may have a second height H2 in a direction perpendicular to the center axis of the mixing part 1100 based on the inlet hole IH.

A distance of the guide plate 1610 may mean a distance from the center portion of the mixing part 1100 when the guide plate 1610 is disposed in the mixing part 1100. As an example, the first plate 1611 may have a first distance D1 from the center axis of the mixing part 1100. At this point, the first distance D1 may be understood as the minimum distance from the center axis of the mixing part 1100 to the first plate 1611, but is not limited thereto. The second plate 1612 may also have a second distance D2 from the center axis of the mixing part 1100.

An inclined angle of the guide plate 1610 may mean an angle with respect to the inlet hole IH while the guide plate 1610 is disposed in the mixing part 1100. As an example, the second plate surface S12 of the first plate 1611 may have a first inclined angle IA1 on the basis of a surface including the inlet hole IH or a surface in parallel to the inlet hole IH. Furthermore, the second plate 1612 may also have a second inclined angle IA2.

Referring to FIG. 13(b), the guide plate 1610 may be designed to have a predetermined length.

The length of the guide plate 1610 may be defined in a direction in parallel to the center axis of the mixing part 1100. For example, as shown in FIG. 13(b), the first plate 1611 extends from a first plate end 1611a to a second plate end 1611b, and have a first length L1. At this point, the first length L1 may be understood as a length of a straight line connecting a point of the first plate end 1611a to a point of the second plate end 1611b, among straight lines in parallel to the center axis of the mixing part 1100. The second plate 1612 may also extend from a third plate end to a fourth plate end, and may have a second length.

The height and the distance of the guide plate 1610 may be designed based on an internal structure of the mixing part 1100. However, the mixing part 1100 may have a third height H3 on the basis of the inlet hole IH, and is assumed to have a preset width W. It is assumed that the center axis of the mixing part 1100 is equal to the center axis CA of the refrigerant spray unit 2100.

The height of the guide plate 1610 may be preferably designed to be equal to or higher than a half of the height of the mixing part 1100. For example, the first height H1 of the first plate 1611 and/or the second height H2 of the second plate 1612 may be equal to or higher than a half of the third height H3 of the mixing part 1100. This is to allow the composition to reach the upper portion of the main stream MS of the refrigerant as described above.

The distance of the guide plate 1610 is preferably designed to be equal to or higher than ¼ of the width W of the mixing part. As an example, the first distance D1 of the first plate 1611 and/or the second distance D2 of the second plate 1612 may be equal to or higher than ¼ of the width W of the mixing part. This is because the width of the guide plate 1610 is designed in response to the first distance D1 and the second distance D2, and when the width of the guide plate 1610 is excessively reduced to be smaller than the maximum size of a section of the main stream MS of the refrigerant, the refrigerant spray is degraded, and moreover, the temperature of the refrigerant in the guide plate 1610 is lowered and the composition freezes.

An inclined angle of the guide plate 1610 may be determined between 0° to 90°. As an example, the first inclined angle IA1 of the second plate surface S12 of the first plate 1611 with respect to the inlet hole IH may be determined between 0° to 90°. However, when the first inclined angle IA1 is 0°, the first plate surface S11 and the second plate surface S12 are substantially in parallel to each other, and it is necessary to provide an additional surface between the first plate surface S11 and the second plate surface S12. The second inclined angle IA2 of the second plate 1612 may also be described as described in the first inclined angle IA1.

The length of the guide plate 1610 may be shorter than the length of the inner surface of the mixing part 1100 but is not limited thereto. As an example, the first length L1 of the first plate 1611 may be shorter than the distance from the first end 1100*a* to the second end 1100*b* of the mixing part 1100. The length of the guide plate 1610 may be equal to or higher than a predetermined value in consideration of the degree of spreading of the composition introduced through the inlet hole IH.

Meanwhile, when the guide plate 1610 is used, the composition used for spray needs to have a relatively high freezing point. This is because the temperature of the guide plate 1610 may be reduced by the sprayed refrigerant and therefore the temperature of the composition moved over the guide plate 1610 is also lowered to result a problem in that the frozen composition is sprayed.

Figure 14:
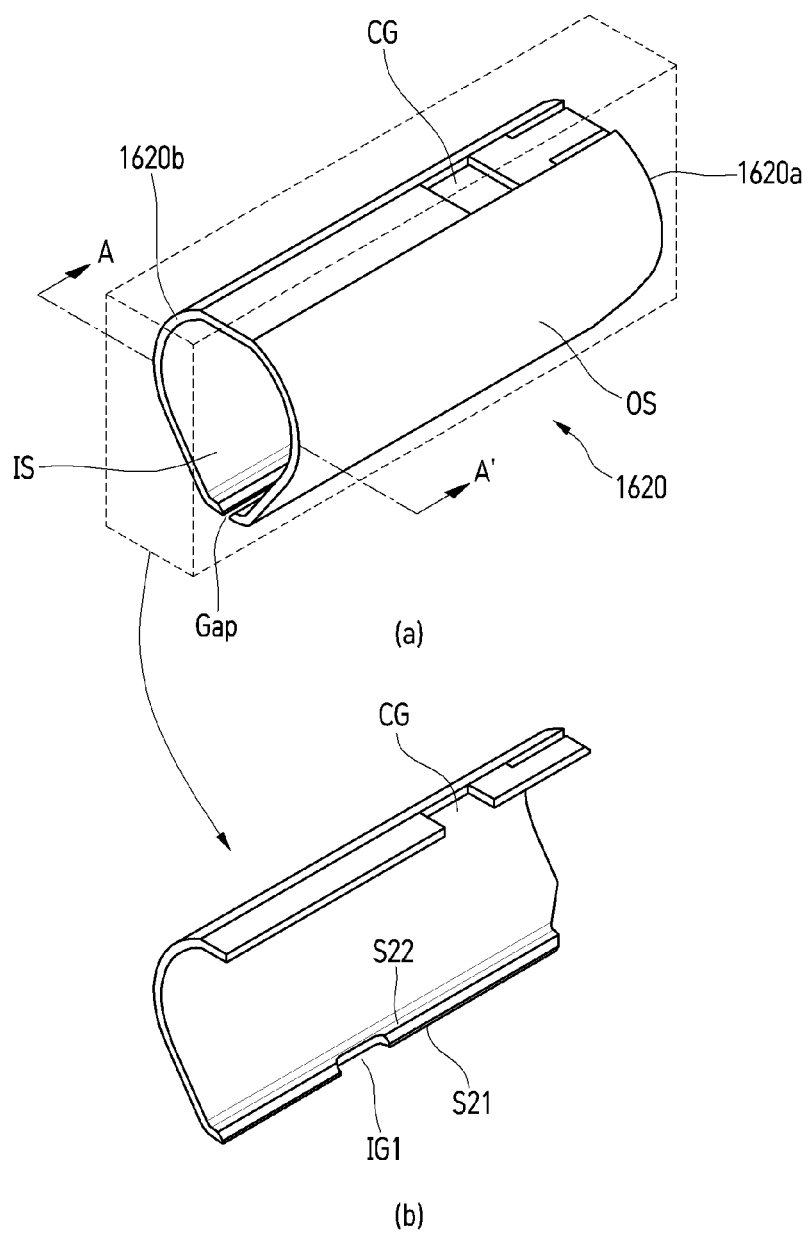
FIG. 14 is a view showing a spreading film according to one embodiment.

FIG. 14 is a view showing a spreading film 1620 according to one embodiment.

Referring to FIG. 14, the spreading film 1620 may extend from a first film end 1620*a* to a second film end 1620*b*, and may include an inner surface IS and an outer surface OS.

The spreading film 1620 may be attached to and detached from the mixing part 1100 of the mixing module 1000. Otherwise, the spreading film 1620 may be implemented to be integrated with the mixing part 1100 so that the spreading film 1620 may constitute a part of the mixing part 1100.

The spreading film 1620 may be manufactured with the bent or curved plate, but the specification is not limited thereto.

The outer surface OS of the spreading film 1620 may include a contact portion. The contact portion may mean a portion where the spreading film 1620 is in contact with the inner surface of the mixing part 1100 when the spreading film 1620 is mounted to the mixing part 1100.

The contact portion of the spreading film 1620 may include a first film surface S21. The first film surface S21 may be understood as the same component as the first plate surface S11 of the guide plate 1610 described above. As an example, when the spreading film 1620 is disposed close to the inlet hole IH, the first film surface S21 may be in contact with the inner surface of the mixing part 1100. The first film surface S21 and the inner surface of the mixing part 1100 may be in planar-contact or linear-contact with each other.

The inner surface IS of the spreading film 1620 may include an inclined portion. The inclined portion may mean a portion on which the composition is moved over. The outer surface OS and the inner surface IS of the spreading film 1620 may face each other.

The inclined portion of the spreading film 1620 may include a second film surface S22. The second film surface S22 is a surface that is inclined at a preset angle with respect to the inlet hole IH when the spreading film 1620 is disposed at the mixing part 1100, and may be understood as a surface inducing movement of the composition. In other words, the second film surface S22 may have a preset angle with respect to a flat surface including the inlet hole IH. At this point, the first film surface S21 and the second film surface S22 may have a specific angle therebetween.

The first film surface S21 and the second film surface S22 may be directly and indirectly connected to each other.

The first film surface S21 and the second film surface S22 may meet each other. In other words, the first film surface S21 and the second film surface S22 may be folded from each other and may share one edge.

The first film surface S21 and the second film surface S22 do not meet each other, and in this case, an additional surface may exist between the first film surface S21 and the second film surface S22. At this point, a flat surface including the first film surface S21 and a flat surface including the second film surface S22 may meet each other or may be in parallel to each other. Otherwise, the first film surface S21 and the second film surface S22 may face each other.

The spreading film 1620 may include a third film surface and a fourth film surface. The description of the first film surface S21 may be equally applied to the third film surface, and the description of the second film surface S22 may be equally applied to the fourth film surface. However, the first film surface and the third film surface may be symmetric to each other on the basis of a center axis of the spreading film 1620, and the second film surface and the fourth film surface may be symmetric to each other on the basis of a center axis of the spreading film 1620.

The composition introduced through the inlet hole IH may be moved over the inner surface IS by adhesion with the inner surface IS.

The outer surface OS of the spreading film 1620 may be composed of one curved surface, a plurality of flat surfaces, a plurality of curved surfaces, or combination thereof. Likewise, the inner surface IS of the spreading film 1620 may be composed of one curved surface, a plurality of flat surfaces, a plurality of curved surfaces, or combination thereof.

Figure 15:
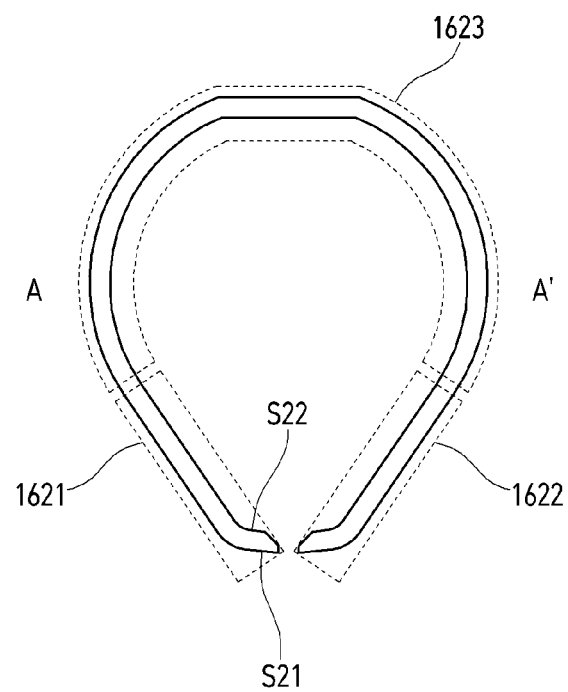
FIG. 15 is a view showing a front surface of the spreading film according to one embodiment.

FIG. 15 is a view showing a front surface of the spreading film 1620 according to one embodiment.

Referring to FIG. 15, the spreading film 1620 may include a first portion 1621, a second portion 1622, and a third portion 1623. For the convenience of description, each of the first to third portions 1621, 1622, and 1623 is an expression used to refer to a part of the spreading film 1620, and may be called by first to third plates, first to third frames, first to third structures, or the like.

The first portion 1621 and the second portion 1622 may be understood to respectively correspond to the first plate 1611 and the second plate 1612 of the guide plate 1610. Specifically, the first portion 1621 and the second portion 1622 may be located with the inlet hole IH located therebetween, and the composition introduced through the inlet hole IH may be moved to the main stream MS of the refrigerant while riding on the first portion 1621 or the second portion 1622.

Unlike the guide plate 1610, the spreading film 1620 may include the third portion 1623 connecting the first portion 1621 and the second portion 1622 to each other. In other words, the first to third portions 1621, 1622, and 1623 may be formed in a physically integral body.

The third portion 1623 may have an arch form. The third portion 1623 may be composed of one curved surface, a plurality of flat surfaces, a plurality of curved surfaces, or combination thereof.

As described below, the third portion 1623 may induce the composition to be more evenly mixed to the spray stream of the refrigerant.

Figure 16:
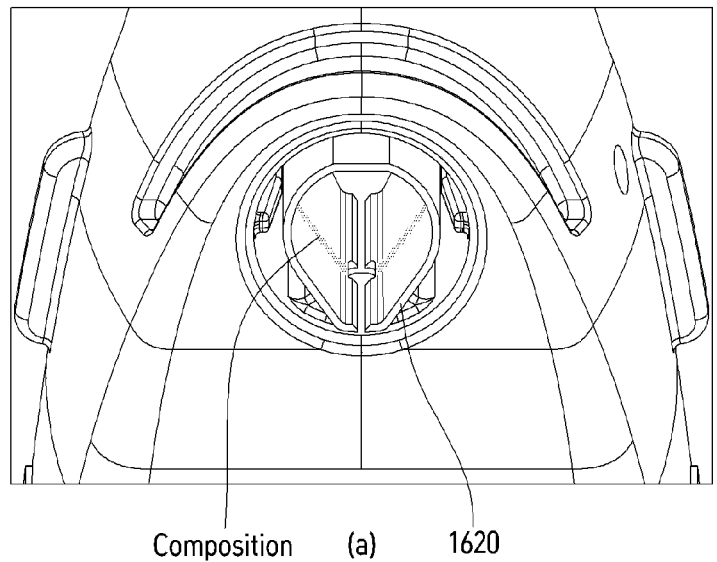
FIG. 16 is a view showing a process in which the composition is moved through the spreading film according to one embodiment.
Figure 16:
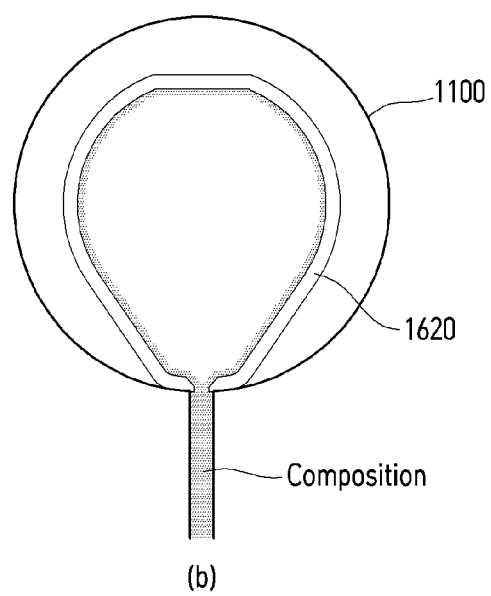

FIG. 16 is a view showing a process in which the composition is moved through the spreading film 1620 according to one embodiment.

Referring to FIG. 16, the composition introduced through the inlet hole IH may be moved on the first portion 1621 to reach the third portion 1623 or may be moved on the second portion 1622 to reach the third portion 1623.

The composition may be moved in order of the first portion 1621-the third portion 1623-the second portion 1622 or in order of the second portion 1622-the third portion 1623-the first portion 1621, to be rotated on the basis of the center axis of the spreading film 1620. Rotation of the composition may allow the composition to be evenly distributed in the spray stream of the refrigerant.

Moreover, the third portion 1623 may prevent the composition from being moved out of the main stream MS of the refrigerant.

The spreading film 1620 may be manufactured by bending a flat plate as described above. As an example, the spreading film 1620 may be manufactured by a step of preparing a square plate having a first edge and a second edge that face each other and a step of curving the square plate such that the first edge and the second edge face each other. At this point, the first edge and the second edge may constitute the outer surface OS, and may be included in the contact portion.

Meanwhile, when the spreading film 1620 is manufactured as described above, as shown in FIG. 14, a gap may be formed between the first portion 1621 and the second portion 1622 of the spreading film 1620. When the spreading film 1620 is manufactured in a form injecting metal or the like in a specific shape, the first portion 1621 and the second portion 1622 may be directly connected to each other and a gap therebetween may not be formed.

As shown in FIG. 14 again, the spreading film 1620 may include an inlet groove and a fastening groove CG.

The inlet groove is a groove corresponding to the inlet hole IH, and may include a first inlet groove IG1 formed in the first portion 1621 and a second inlet groove formed in the second portion 1622.

The spreading film 1620 may be fastened to an inner portion of the mixing part 1100 through the fastening groove CG. A connection member (e.g., hook member) may be formed in the mixing part 1100 to correspond to the fastening groove CG. The fastening groove CG may be formed in the third portion 1623 of the spreading film 1620, but is not limited thereto.

The spreading film 1620 may have a preset radius of curvature.

Figure 17:
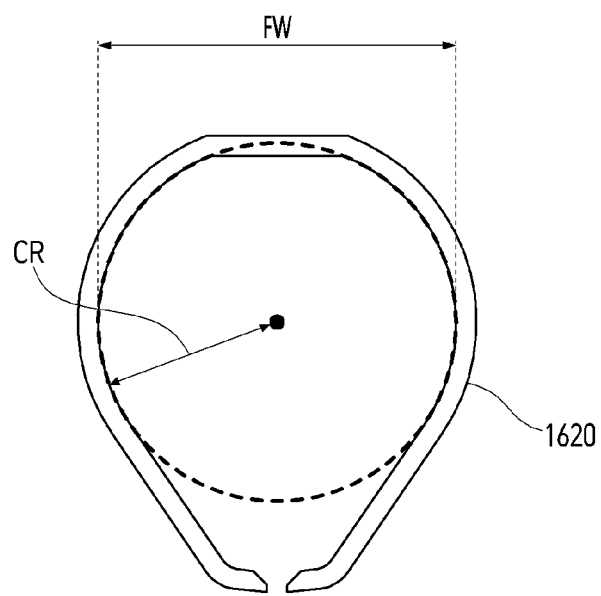
FIG. 17 is a view showing a radius of curvature of the spreading film according to one embodiment.

FIG. 17 is a view showing a radius of curvature CR of the spreading film 1620 according to one embodiment. Referring to FIG. 17, a part of the inner surface IS of the spreading film 1620 may have the radius of curvature CR. The radius of curvature CR may be understood as a radius of curvature CR of a portion of corresponding to the third portion 1623 among the inner surface IS of the spreading film 1620.

The radius of curvature CR may be designed to be less than the width W of the mixing part and equal to or greater than ¼ of the width W. However, when a section of the mixing part 1100 is not a circle and is an oval, the mixing part 1100 may be differently designed, and the mixing part 1100 may be experimentally determined in order to correspond to the maximum size of the section of the main stream MS of the refrigerant.

As an example, for the mixing part 1100 providing a mixing space having a specific form, while the radius of curvature CR is changed, experiments observing a spot size of the refrigerant sprayed from the mixing module 1000, and whether or not the composition freezes are performed, and the optimum value of the radius of curvature CR may be experimentally determined.

The spreading film 1620 may have a film width FW. The film width FW may be understood as the horizontal maximum width of the spreading film 1620. As an example, the film width FW may be twice the radius of curvature CR.

Meanwhile, the spreading film 1620 may have a predetermined length. The length of the spreading film 1620 may be understood to be equal to the first length L1 of the guide plate 1610 described above.

Figure 18:
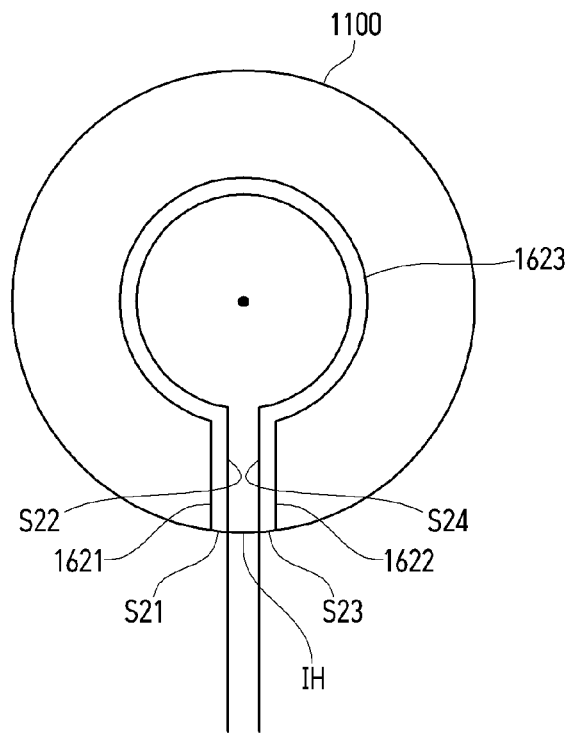
FIG. 18 is a view showing a spreading film according to another embodiment.

FIG. 18 is a view showing the spreading film 1620 according to one embodiment.

The spreading film 1620 may be implemented such that a section thereof is shaped in a keyhole. Specifically, as shown in FIG. 18, the first portion 1621 of the spreading film 1620 may include the first film surface S21 in contact with the inlet hole IH and the second film surface S22 substantially perpendicular to a section of the inlet hole IH. Likewise, the second portion 1622 of the spreading film 1620 may include the third film surface S23 in contact with the inlet hole IH and the fourth film surface S24 substantially perpendicular to a section of the inlet hole IH.

In addition to this, the spreading film 1620 may have various forms. As an example, the spreading film 1620 may have a form in which a width thereof narrows or widens in a direction from the first film end 1620a to the second film end 1620b. Also, a sectional form of the spreading film 1620 may be implemented variously such as a circular shape, an oval shape, a polygonal shape, or a figure composed of combination of a linear line and a curved line.

Figure 19:
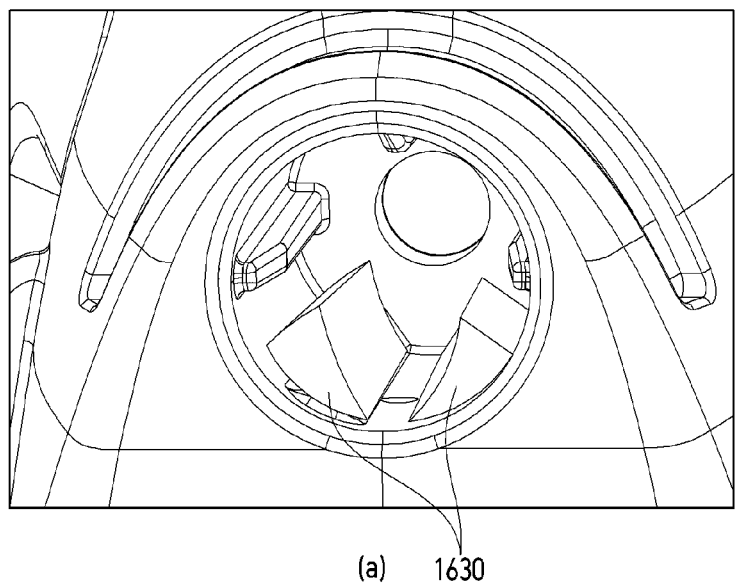
FIG. 19 is a view showing various shapes of a guide member according to one embodiment.
Figure 19:
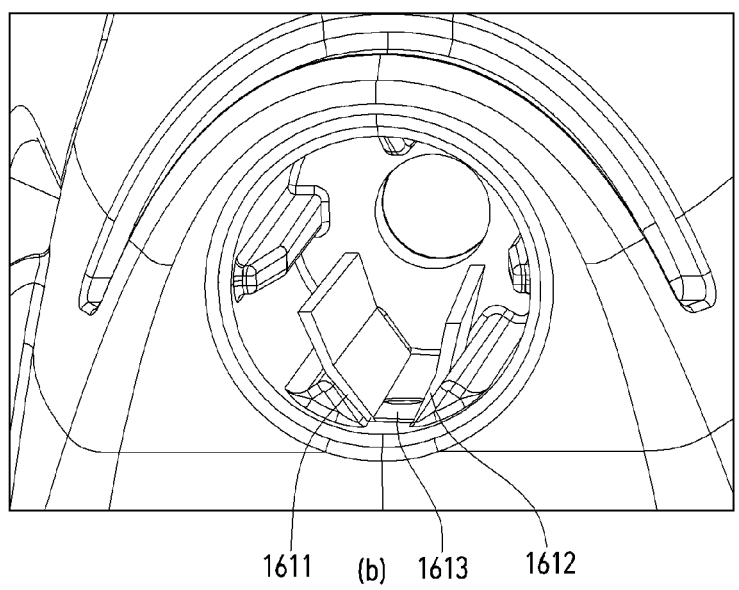

FIG. 19 is a view showing various shapes of a guide member according to one embodiment.

Referring to FIG. 19(a), guide walls 1630 may protrude from the inner surface of the mixing part 1100. Specifically, the guide walls 1630 may be formed on both sides with the inlet hole IH interposed, and surfaces of the guide walls 1630 may be designed to be equal to the second plate surface S12 of the first plate 1611 and the fourth plate surface S14 of the second plate 1612 that are described above. At this point, based on the inlet hole IH, the height of the guide walls needs to be designed to be equal to or higher than a ½ of the second height H2 of the mixing part 1100.

Referring to FIG. 19(b), the guide plate 1610 may further include a third plate 1613. The third plate 1613 may connect the first plate 1611 and the second plate 1612 to each other so that a gap does not exist between the first plate 1611 and the second plate 1612. The third plate 1613 may have a hole corresponding to the inlet hole IH. As the guide plate 1610 further includes the third plate 1613, the composition introduced through the inlet hole IH may be moved to the first plate 1611 or the second plate 1612 through the third plate 1613. In other words, there is an advantage that the composition can be moved to the main stream MS of the refrigerant over the guide plate 1610 not only the side direction but also all directions.

4.3. Possible Problem #3 and Solution Plan

When a freezing point of the composition is relatively high, the temperature of the main stream MS of the refrigerant is relatively low, and thus the frozen composition can be sprayed, which has been described above.

In order to solve the problem in that the composition freezes, a method in which heat is applied into the mixing part 1100 to increase the temperature of the mixing part 1100 or a method in which the temperature of the composition is directly increased can be considered. However, the methods may cause deterioration of the cooling effect of the refrigerant or the quality degradation or the increase of manufacturing costs of a product due to the need for an additional heating device.

Hereinbelow, referring to FIGS. 20 to 23, a design direction of the mixing module 1000 that prevents the freezing of the composition without inhibiting the cooling effect as much as possible and without using a separate device will be described.

The basic principle is as follows. The internal space of the mixing part 1100 is divided into a region corresponding to the main stream MS of the refrigerant and other regions, and regions in which external air having relatively high temperature compared to the refrigerant is separated are continuously circulated, so that freezing of the composition can be prevented.

Figure 20:
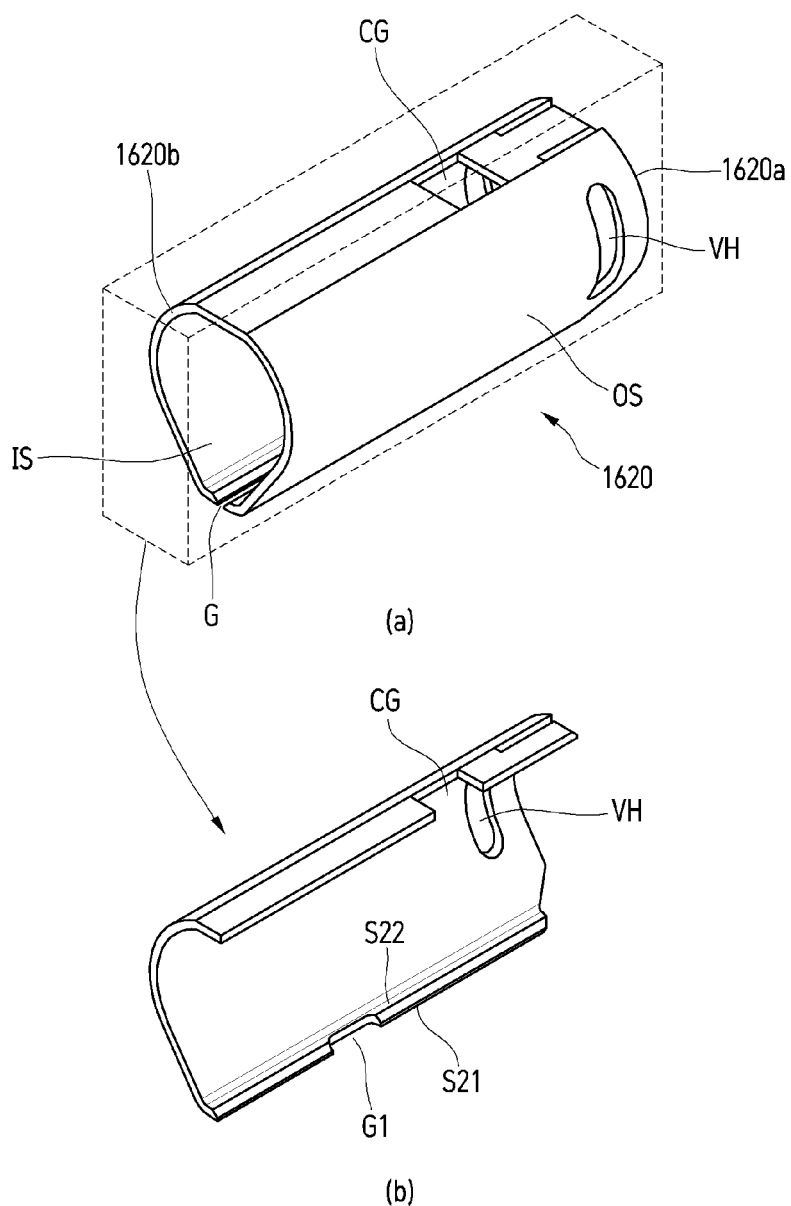
FIG. 20 is a view showing the spreading film having a vent hole according to one embodiment.

FIG. 20 is a view showing the spreading film 1620 having a vent hole VH according to one embodiment.

Figure 21:
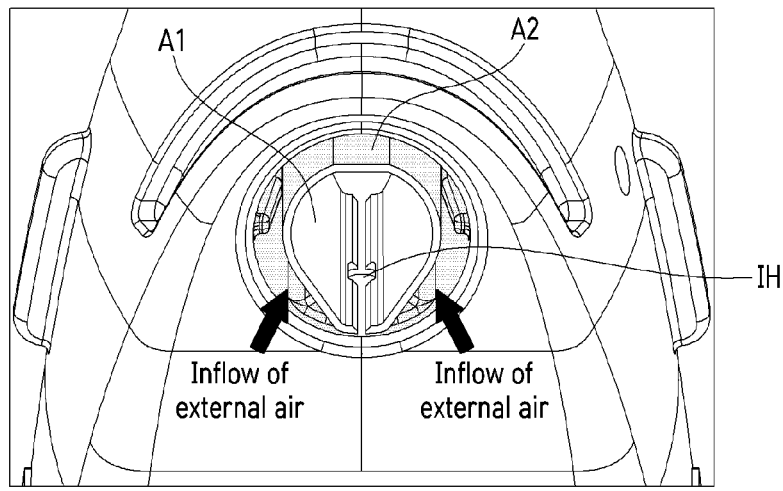
FIG. 21 is a view showing a process in which external air is introduced into the mixing module to be circulated according to one embodiment.
Figure 21:
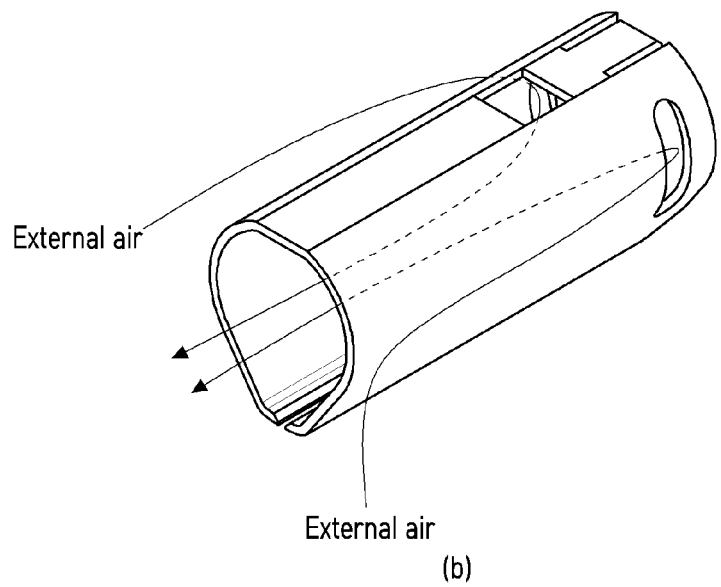

FIG. 21 is a view showing a process in which external air is introduced into the mixing module 1000 to be circulated according to one embodiment.

Figure 22:
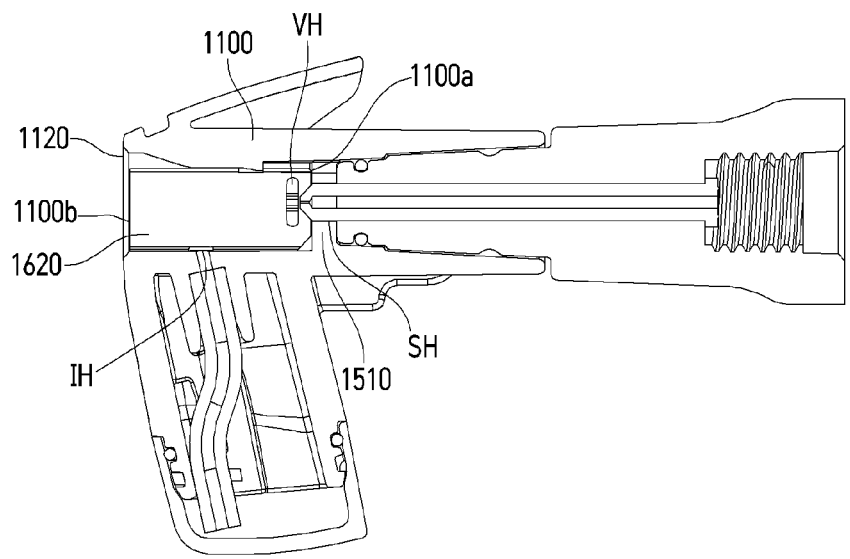
FIG. 22 is a sectional view showing the mixing part to which the spreading film is mounted according to one embodiment.

FIG. 22 is a sectional view showing the mixing part 1100 to which the spreading film 1620 is mounted according to the embodiment.

As shown in FIG. 20, the spreading film 1620 described in FIG. 14 is used, and the vent hole VH may be formed in the spreading film 1620.

Referring to FIG. 21, when the spreading film 1620 is mounted to the mixing part 1100, the internal space of the mixing part 1100 may be divided into a first region A1 inside the spreading film 1620 and a second region A2 outside the spreading film 1620. At this point, the first region A1 may be understood as a region in which the main stream MS of the refrigerant is located. As the refrigerant is sprayed, the pressure of the internal space of the mixing part 1100 is entirely lowered, so that air outside of the mixing part 1100 may be introduced into the mixing part 1100. At this point, as the refrigerant is sprayed in the first region A1, external air may be introduced into the second region A2 rather than the first region A1 as shown in FIG. 21(*a*).

As shown in FIG. 21(*b*), external air introduced into the second region A2 may be moved to the vent hole VH formed in the spreading film 1620. This means that the closer the vent hole VH is formed to the first film end 1620*a* of the spreading film 1620, the more the external air may be moved to the internal space of the mixing part 1100 or the vicinity of the refrigerant spray hole 2110.

Then, the external air may be introduced into the first region A1 through the vent hole VH and as a result the external air may be discharged out of the mixing part 1100 together with the refrigerant.

In other words, by the vent hole VH formed in the spreading film 1620, the external air having relatively high temperature than the refrigerant may be continuously circulated to the second region A2-the vent hole VH-the first region A1, and the circulated external air may supply heat to the spreading film 1620 while passing through the outer surface OS of the spreading film 1620.

The spreading film 1620 may be supplied with heat from the external air and transmit the heat to the composition moved over the spreading film 1620. The composition may be sprayed without freezing as heat is transferred thereto.

Referring to FIG. 20 again, the vent hole VH may be formed close to the first film end 1620*a* rather than the second film end 1620*b* of the spreading film 1620. Moreover, the vent hole VH may be formed close to the first film end 1620*a* rather than a middle point between the first film end 1620*a* and the second film end 1620*b* of the spreading film 1620. Accordingly, the external air may be discharged after being moved to the internal space of the mixing part 1100, and accordingly the spreading film 1620 may be supplied with heat from the external air overall.

Referring to FIG. 22, in a state in which the spreading film 1620 is mounted to the mixing part 1100, the vent hole VH may be located close to the first end 1100*a* rather than the second end 1100*b* of the mixing part 1100. Otherwise, the vent hole VH may be located between the inlet hole IH and the first end 1100*a*. Otherwise, the vent hole VH may be located between the inlet hole IH and the first end 1100*a*, and may be located close to the first end 1100*a* rather than the inlet hole IH.

The vent hole VH may be formed at each of left and right portions of the spreading film 1620. Otherwise, the vent hole VH may be formed at one of the left or right portion the spreading film 1620.

The vent hole VH may be implemented in various forms. As an example, the vent hole VH may have a circular form, a polygonal form, or an oval form.

As described above, in order to allow the spreading film 1620 to be supplied with heat from the external air, and to transmit the supplied heat to the composition, the heat conductivity of the spreading film 1620 needs to be equal to or higher than a predetermined value.

In the heat conductivity, as a result of experiments using various metals, copper (Cu), aluminum (Al), and steel use stainless (SUS) do not cause the freezing of the composition. Therefore, according to an example, the spreading film 1620 may be composed of copper (Cu), aluminum (Al), steel use stainless (SUS), or combination thereof. Otherwise, as another example, the heat conductivity of the spreading film 1620 may be higher than the heat conductivity of SUS. Specifically, the spreading film 1620 may have the heat conductivity equal to or higher than 12 W/m·K.

Furthermore, in order to efficiently perform heat transmission of the spreading film 1620, the thickness of the spreading film 1620 also needs to be less than or equal to a predetermined value. As an example, the thickness of the spreading film 1620 may be approximately less than or equal to 1.0 mm. Preferably, the thickness of the spreading film 1620 may be less than or equal to 0.5 mm. More preferably, the thickness of the spreading film 1620 may be approximately 0.3 mm.

Meanwhile, even when the vent hole VH is not formed in the spreading film 1620, circulation of external air may be induced.

Figure 23:
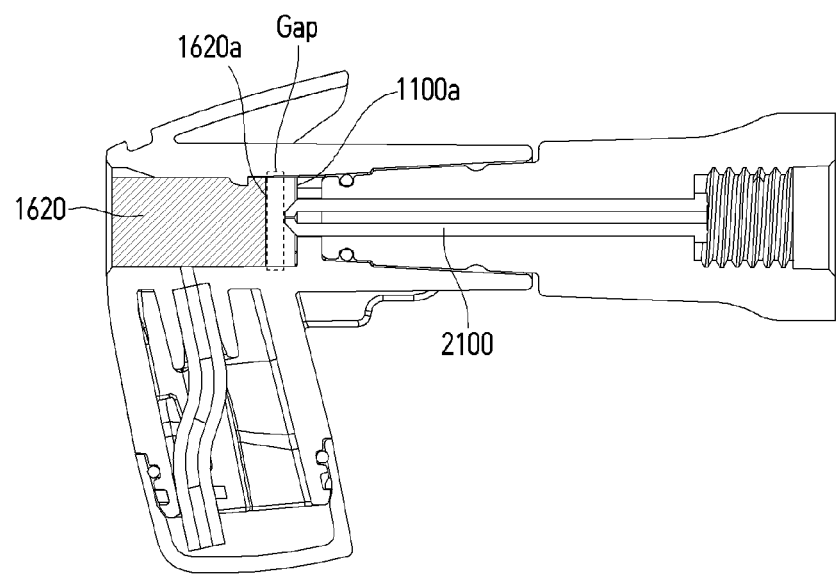
FIG. 23 is a view showing a state in which the spreading film is disposed at the mixing part to form a gap between the spreading film and a refrigerant spray hole according to one embodiment.

FIG. 23 is a view showing a state in which the spreading film 1620 is disposed at the mixing part 1100 to form a gap between the spreading film 1620 and the refrigerant spray hole 2110 according to one embodiment.

Referring to FIG. 23, the spreading film 1620 may be disposed in the mixing part 1100 so that a gap is formed between the first film end 1620*a* of the spreading film 1620 and the refrigerant spray hole 2110. For example, when the spreading film 1620 is disposed in the mixing part 1100, the first film end 1620*a* of the spreading film 1620 may be spaced apart from the refrigerant spray hole 2110 in the distal direction (e.g., spray direction of refrigerant) by a preset distance. Otherwise, the first film end 1620*a* may be spaced apart from the first end 1100*a* of the mixing part 1100 in the distal direction by a preset distance.

Meanwhile, a form of the first film end 1620*a* of the spreading film 1620 may be designed to form a space between the spreading film 1620 and the first end 1100*a* when the spreading film 1620 is disposed in the mixing part 1100.

At this point, the length of the spreading film 1620 may be shorter than the length of the mixing part 1100 but is not limited thereto.

A gap or a space formed between the spreading film 1620 and the first end 1100*a* of the mixing part 1100 or the refrigerant spray hole 2110 may serve as the vent hole VH described above.

4.4. Selective Use of the Guide Member

As described above, the guide member may solve problems that may occur when the refrigerant and the composition are mixed and sprayed in the mixture spray system 100.

A form of the guide member to solve any problem may be various, and according to the property of the composition, the guide member having a desired form may be used (e.g., form mounted to or integrated with the mixing module 1000). As an example, when the viscosity and the cohesion of the composition are relatively low and the freezing point is relatively low, the guide member may not be used. As another example, when the viscosity and the cohesion of the composition is relatively high and the freezing point is relatively low, the guide plate 1610, the spreading film 1620, or the spreading film 1620 having the vent hole VH may be used. As another example, when the freezing point of the composition is relatively high, the spreading film 1620 having the vent hole VH may be used.

5. Connection of the Mixing Module and the Refrigerant Providing Device

Hereinbelow, a process of coupling the mixing module 1000 and the refrigerant providing device 2000 to each other and components required thereto will be described with reference to FIGS. 24 and 25. Furthermore, a component for the guide member to be mounted to the mixing module 1000 will be described with reference to FIG. 26.

Figure 24:
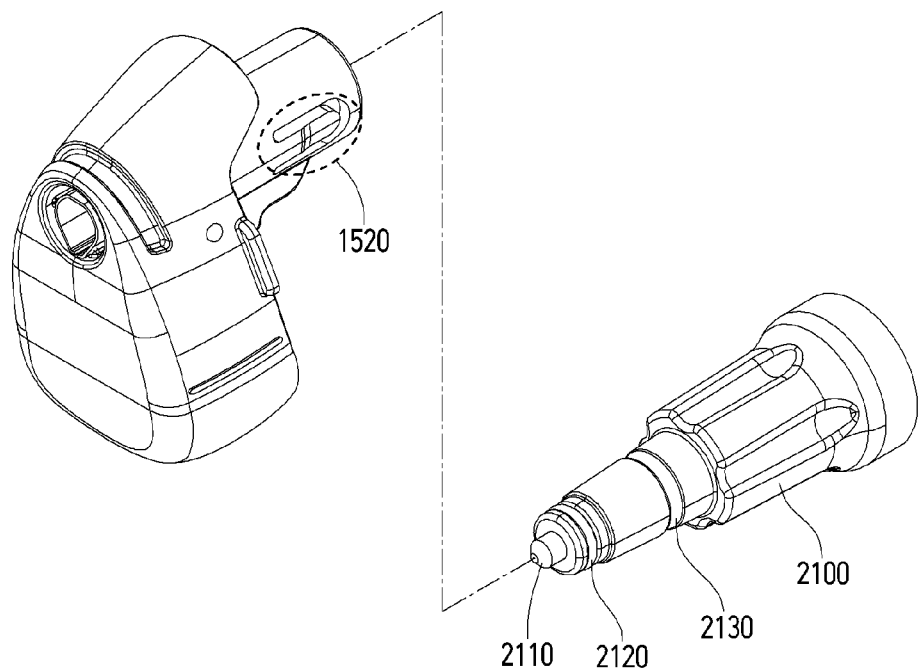
FIG. 24 is a view showing a process in which the mixing module is mounted to the refrigerant spray unit according to one embodiment.

FIG. 24 is a view showing a process in which the mixing module 1000 is mounted to the refrigerant spray unit 2100 according to one embodiment.

Referring to FIG. 24, the mixing module 1000 may include a first fastening member 1520, and the refrigerant spray unit 2100 may include a second fastening member 2130.

The first fastening member 1520 may be formed in the fastening part 1500 of the mixing module 1000. The first fastening member 1520 may be a hook member. Otherwise, the first fastening member 1520 may include a locking protrusion.

The second fastening member 2130 may be formed in an outer surface of the refrigerant spray unit 2100. The second fastening member 2130 may include a groove or a hole.

The first fastening member 1520 of the mixing module 1000 and the second fastening member 2130 of the refrigerant spray unit 2100 may be coupled to each other. As an example, as the refrigerant spray unit 2100 is inserted into the mixing module 1000 in a sliding manner, the locking portion of the first fastening member 1520 may be caught by the groove of the second fastening member 2130.

The refrigerant spray unit 2100 may include an O-ring 2120. The O-ring 2120 may strengthen coupling between the refrigerant spray unit 2100 and the mixing module 1000, and may serve a sealing function as described below. The O-ring 2120 may be located between the refrigerant spray hole 2110 and the second fastening member 2130. Accordingly, indiscriminate separation of the mixing module 1000 from the refrigerant spray unit 2100 may be prevented.

Figure 25:
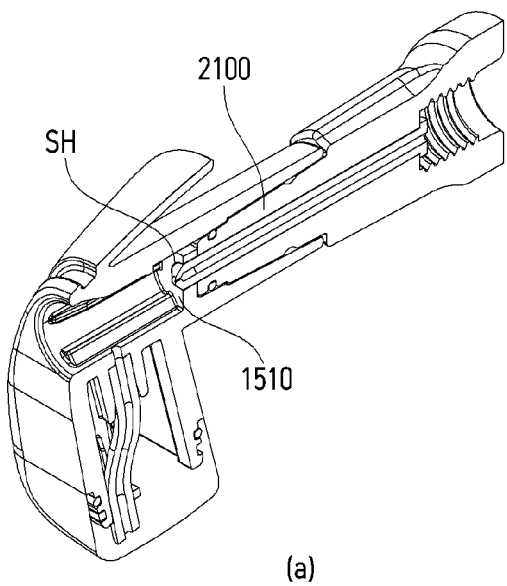
FIG. 25 is a view showing a process in which sealing is performed when the mixing module is coupled to the refrigerant spray unit according to one embodiment.
Figure 25:
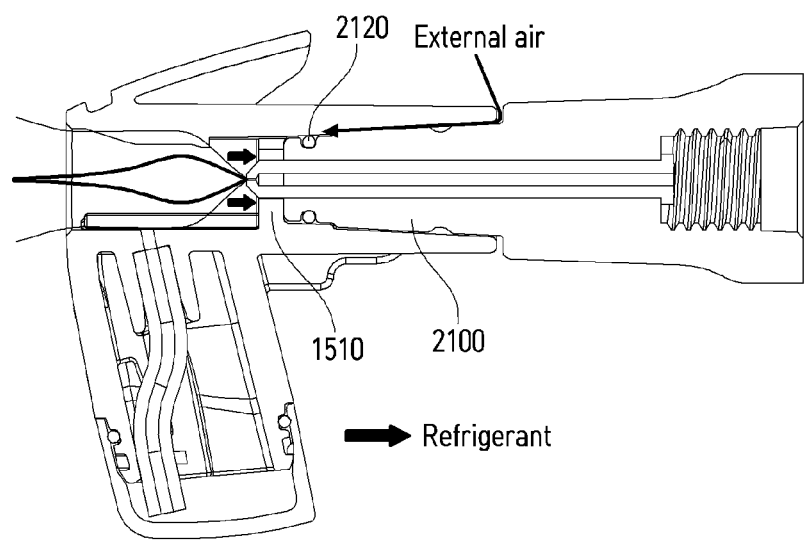

FIG. 25 is a view showing a process in which sealing is performed when the mixing module 1000 is coupled to the refrigerant spray unit 2100 according to one embodiment.

Referring to FIG. 25, when the refrigerant spray unit 2100 is inserted into the mixing module 1000, a front portion (portion including the refrigerant spray hole 2110) of the refrigerant spray unit 2100 is inserted into the insertion hole SH of the support 1510, and thus the support 1510 may support the refrigerant spray hole 2110.

Meanwhile, when the refrigerant is sprayed from the refrigerant spray unit 2100, some of the refrigerant may flow backwards reverse to the spray direction of the refrigerant in the mixing part 1100. The support 1510 may prevent the refrigerant flowing backwards from reaching the refrigerant spray unit 2100.

Furthermore, referring to FIG. 25(*b*), the O-ring 2120 of the refrigerant spray unit 2100 may prevent external air from being introduced into a gap between the mixing module 1000 and the refrigerant spray unit 2100.

As described above, the support 1510 and the O-ring 2120 reduce a risk due to the refrigerant flowing backwards or inflow of external air to improve stability of fastening between the mixing module 1000 and the refrigerant spray unit 2100.

Figure 26:
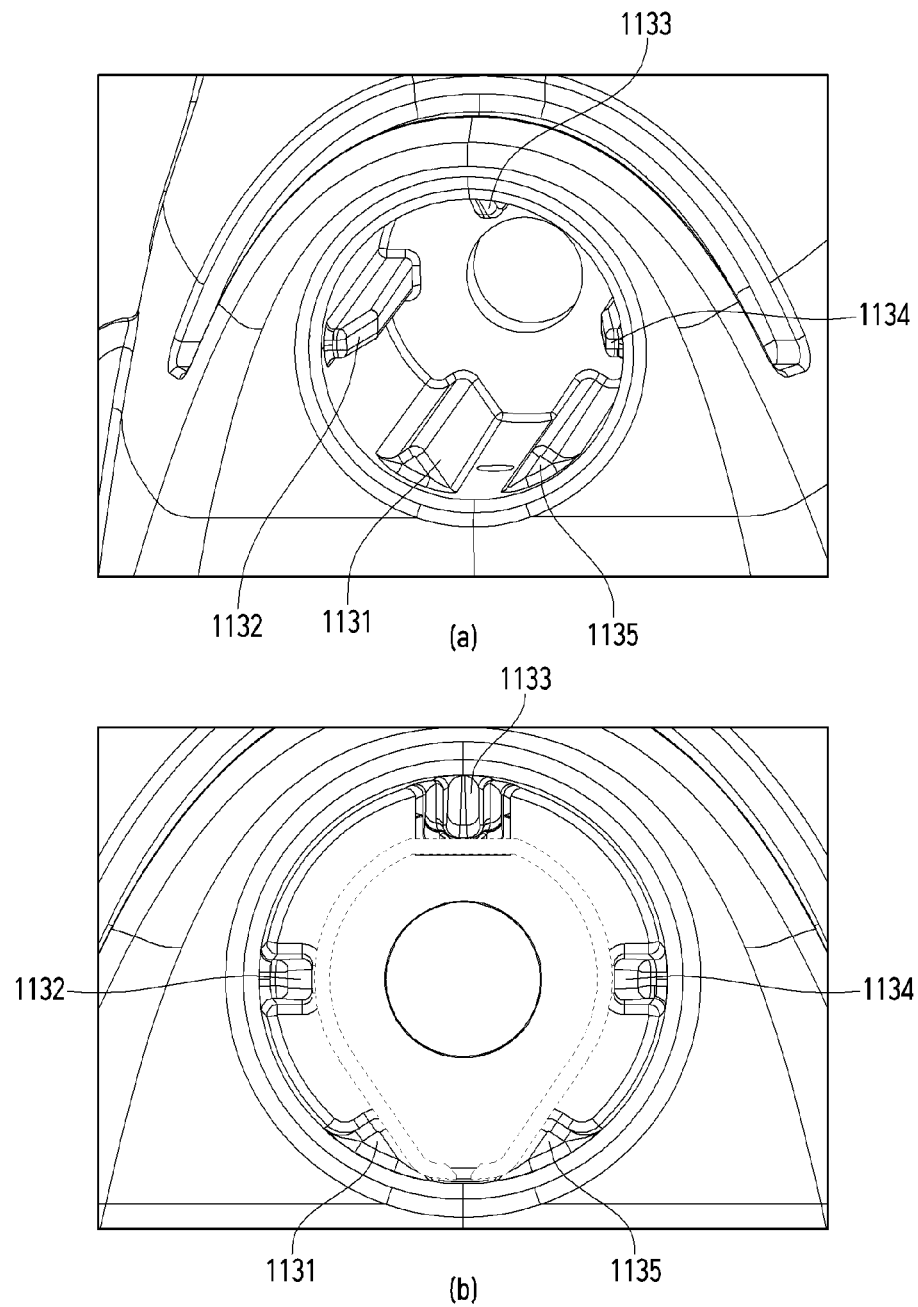
FIG. 26 is a view showing the component of the guide member to be mounted to the mixing module according to one embodiment.

FIG. 26 is a view showing the configuration of the guide member 1000 to be mounted to the mixing module according to one embodiment. Hereinbelow, the specification is described that the guide member is the spreading film 1620, but the technical idea of the specification is not limited thereto.

The mixing module 1000 may include at least one protrusion. As an example, referring to FIG. 26, first to fifth protrusions 1131, 1132, 1133, 1134, and 1135 may be included in the inner portion of the mixing part 1100.

The protrusions may be understood as components serving to support a specific object such as a rib or a rail.

The protrusion may support the spreading film 1620. Specifically, the protrusions may support the spreading film 1620 from shaking in the mixing part 1100. As an example, when the spreading film 1620 is mounted to the mixing module 1000, the first protrusion 1131 supports the first portion 1621 of the spreading film 1620, and the second to fourth protrusions 1132, 1133, and 1134 support the third portion 1623 of the spreading film 1620, and the fifth protrusion 1135 may support the second portion 1622 of the spreading film 1620.

The protrusions may be designed to correspond to the form of the spreading film 1620.

The plurality of protrusions may be formed symmetrically based on the center axis of the mixing part 1100, but is not limited thereto.

Each protrusion may have a specific length in the parallel direction to the center axis of the mixing part 1100 in the mixing part 1100. The length of protrusion may be shorter than the length of the inner portion of the mixing part 1100.

6. Design of the Mixing Module in Consideration of the Spray Amount

As described above, in the mixture spray system 100, the composition may be moved by negative pressure formation according to spray of the refrigerant. As a result, the amount of spray of the composition partially depends on the amount of spray of the refrigerant.

In this situation, if the amount of the composition or the spray amount of the composition and the amount of the refrigerant or the spray amount of the refrigerant are not precisely controlled, a case in which only the refrigerant may be sprayed due to lack of the composition or a case in which the composition of a required amount (e.g., amount of composition required for one procedure or one treatment) is not all sprayed due to lack of the refrigerant may occur.

In other words, when designing a device spraying the refrigerant and the composition together, 'the identical condition of consumption time' in which the time required for the composition of a specific amount (e.g., ampule capacity) to be consumed and the time required for the refrigerant of a specific amount (e.g., Cartridge capacity) to be consumed are substantially same each other should be satisfied.

Figure 27:
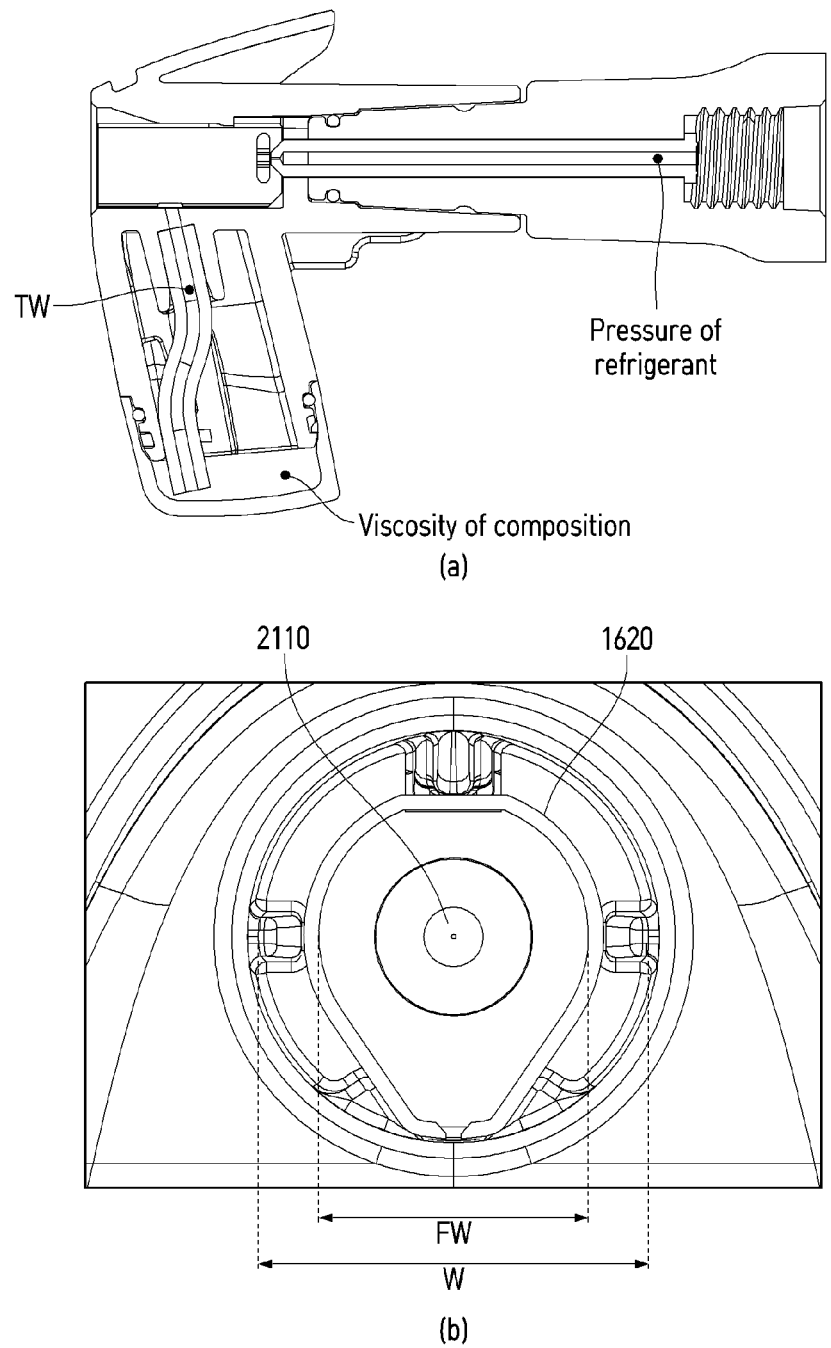
FIG. 27 is a view showing the mixing module in which elements affecting spray amount of the composition are indicated according to one embodiment.

FIG. 27 is a view showing the mixing module 1000 with marked elements affecting spray amount of the composition according to one embodiment.

Referring to FIG. 27, the consumption time of the composition and the consumption time of the refrigerant may be affected by the capacity of the refrigerant cartridge CTR, the refrigerant pressure (e.g., internal pressure of the cartridge CTR), the size of the refrigerant spray hole 2110, the width W of the mixing part, the width of the guide member (e.g., the film width FW), a tube width TW of the tube 1210, and the properties of the composition (e.g., the composition viscosity).

Hereinbelow, for the convenience of description, the specification is described that the guide member is the spreading film 1620, but the technical idea of the specification is not limited thereto.

Among the above-mentioned influencing factors, after values of factors that are difficult to be controlled are specified, values of factors that is possible to be controlled may be designed in consideration of values of the specified factors and 'the identical condition of consumption time'.

First, a type of the composition may be specified. A type of the composition may be specified according to a type of procedure or treatment to be provided. Treatment to be provided is difficult to be arbitrarily changed, so that a type of the composition is also difficult to be changed, and the properties of the composition such as the viscosity of the composition, etc. may be understood as specific values.

Furthermore, the amount of the composition may be determined according to a type of procedure or treatment to be provided or a type of the composition container that is commercially available, and the amount of the refrigerant may be determined according to the capacity of the cartridge CTR. Therefore, the amount of the composition and the amount of the refrigerant are difficult to be arbitrarily controlled, which may be understood as specific values.

Next, the width W of the mixing part may be designed. The width W of the mixing module 1000 may be determined in consideration of the size of the refrigerant providing device 2000, the size of the refrigerant spray unit 2100 or the refrigerant spray hole 2110, and/or the spray amount of the composition. As an example, as the refrigerant providing device 2000 or the refrigerant spray hole 2110 increases, the width W of the mixing part may increase. Meanwhile, as the width W of the mixing part increases, the spray amount of the composition is increases, and therefore, the width W of the mixing part may be readjusted later.

Considering the designed width W of the mixing part, the film width FW of the spreading film 1620 may be designed. The spreading film 1620 may be preferably formed to surround the main stream MS of the refrigerant, and the size of the main stream MS of the refrigerant is changed according to the size of the refrigerant spray hole 2110, and therefore, the film width FW may be designed in consideration of the size of the refrigerant spray hole 2110.

Finally, the tube width TW may be designed. At this point, as the tube width TW increases, the spray amount of the composition increases, which may be considered.

In order to design the mixing module 1000 that satisfies the identical condition of consumption time, some of the above-mentioned variables are set as independent variables, and while changing the independent variables, experiments may be conducted to monitor whether the identical condition of consumption time is satisfied.

The mixing module 1000 or the spreading film 1620 may be designed using values of the variables calculated in the conducted experiments.

As an example, in the state in which the capacity of the cartridge CTR, the pressure of the refrigerant, the size of the refrigerant spray hole 2110, the width W of the mixing part, and the film width FW are fixed as specific values and the type of the composition and the required use amount of the composition is determined, while changing the tube width TW, whether the consumption time of the refrigerant and the consumption time of the composition are substantially the same is monitored, and a value of the tube width TW when the identical condition of consumption time is satisfied may be calculated.

The mixing module 1000 may be designed to have the calculated value of the tube width TW and the specified width W of the mixing part, and the spreading film 1620 may be designed to have the specified film width FW.

As another example, in the state in which the capacity of the cartridge CTR, the pressure of the refrigerant, the size of the refrigerant spray hole 2110, the width W of the mixing part, and the tube width TW are fixed as specific values and the type of the composition and the required use amount of the composition is determined, while changing the film width FW, whether the consumption time of the refrigerant and the consumption time of the composition are substantially the same is monitored, and a value of the film width FW when the identical condition of consumption time is satisfied may be calculated.

The spreading film 1620 may be designed to have the calculated film width FW, and the mixing module 1000 may be designed to have the specified tube width TW and the specified width W of the mixing part.

7. Cover Design

Hereinafter, a cover COV designed to protect the sensor unit 2600 of the refrigerant providing device 2000 will be described with reference to FIG. 28.

FIG. 28 is a view showing a process in which a cover and mixing module are sequentially coupled to a main body according to one embodiment. Specifically, FIG. 28 (*a*) is a view showing a process in which the cover COV is coupled to the main body (MB), and FIG. 28 (*b*) is a view showing a process in which the mixing module 1000 is coupled to the refrigerant providing device 2000.

Referring to (a) of FIG. 28, a sensing hole SH may be formed in the main body MB. The sensing hole SH is a component that prevents the sensing region SR of the sensor unit 2600 embedded in the main body MB from being blocked. The sensing hole SH may be designed such that the sensing region SR of the sensor unit 2600 passes therethrough. In other words, the sensing path of the sensor unit 2600 may be secured by the sensing hole SH.

Meanwhile, when spraying the composition on the target using the mixture spray system 100, some of the sprayed composition may penetrate the target surface and be absorbed by the target, and some of the sprayed composition may hit the target surface and splash back. Here, there is a possibility that the sensor unit 2600 is contaminated such as the splashing composition being deposited on the sensor unit 2600 through the sensing hole SH.

In addition, the refrigerant providing device 2000 may be independently used for a cooling procedure in which refrigerant is sprayed onto the surface of the target, but as described above, the refrigerant providing device 2000 may be used as the mixture spray system 100 by combining the mixing module 1000. When the refrigerant providing device 2000 is used as the mixture spray system 100, precise temperature control of the target surface may not be essential. In other words, measuring the temperature of the target surface by the sensor unit 2600 may not be performed.

Considering the above, it is necessary to cover the sensing hole SH to prevent contamination of the sensor unit 2600. Referring to (a) of FIG. 28, the cover COV may be designed to include a covering part SP to cover the sensing hole SH.

When the cover COV is coupled to the body MB, the covering part SP of the cover COV may cover at least a portion of the sensing hole SH. For example, in (a) of FIG. 28, the height SPH of the covering part may correspond to the diameter or width of the sensing hole SH. For another example, in (a) of FIG. 28, the height SPH of the covering part may be determined based on the distance between the nozzle 2100 and the sensing hole SH.

Figure 28:
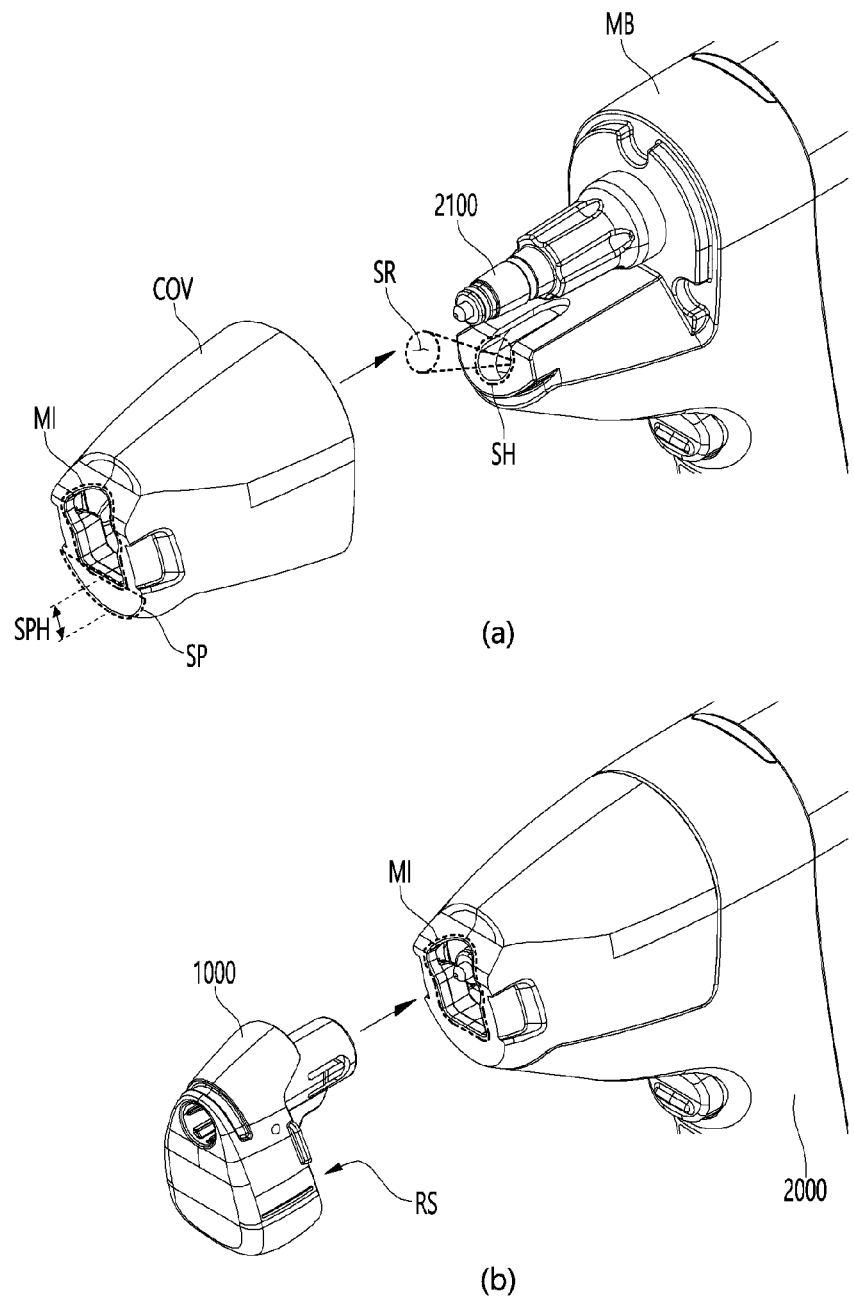
FIG. 28 is a view showing a process in which a cover and the mixing module are sequentially coupled to a main body according to one embodiment.

Referring to (b) of FIG. 28, the sensing hole SH may be covered while the mixing module 1000 is coupled to the refrigerant providing device 2000. Specifically, at least a portion of the sensing hole SH is covered as the cover COV is coupled to the main body MB, but there may be possibility that the composition may flow into the mixing module insertion part MI as the mixing module insertion portion MI is provided in the cover COV. At this time, when the mixing module 1000 is coupled to the refrigerant providing device 2000, the mixing module insertion portion MI of the cover COV may be covered by the rear surface RS of the mixing module 1000. As a result, the sensing hole SH may be completely covered by the covering part SP of the cover COV and the rear surface RS of the mixing module 1000.

8. Example of Using Mixture Spray System

Hereinafter, a process of spraying the refrigerant and the composition using the mixture spray system 100 will be described with reference to FIG. 29.

Figure 29:
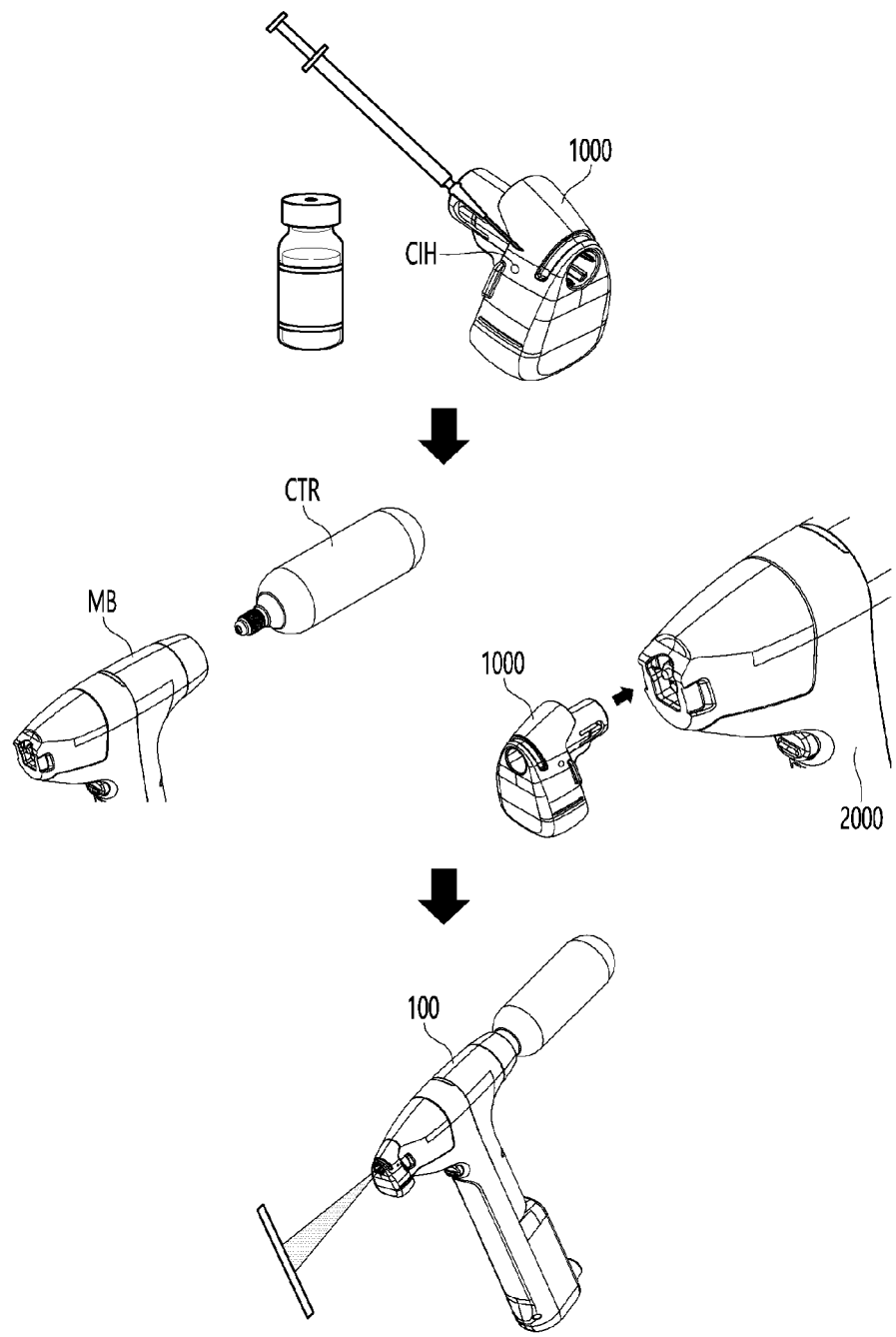
FIG. 29 is a view showing a process of using mixture spray system according to one embodiment.

FIG. 29 is a view showing a process of using mixture spray system according to one embodiment.

First, a user may fill the mixing module 1000 with a composition. For example, referring to FIG. 29, the user may transfer the composition stored in the ampoule to the composition storage part 1300 of the mixing module 1000 using a syringe.

The mixing module may include a composition injection hole CIH fluidly connected to the composition storing part 1300 and through which the injection needle passes.

A user may couple the cartridge CTR in which the refrigerant is stored to the main body MB. As the cartridge CTR is coupled to the cartridge coupling unit 2500 of the main body MB, the sealing part of the cartridge CTR is opened such that the inside of the cartridge CTR and the refrigerant passage in the main body MB can be connected to each other.

A user may couple the mixing module 1000 to the refrigerant providing device 2000.

The order of the combination of the refrigerant providing device 2000 and the mixing module 1000 and the combination of the main body MB and the cartridge CTR may be arbitrarily determined. In other words, the user may combine the cartridge CTR after coupling the mixing module 1000 to the refrigerant providing device 2000, or the user may combine the mixing module 1000 to the refrigerant providing device 2000 after coupling the cartridge CTR to the main body MB.

Meanwhile, the process of filling the mixing module 1000 with the composition may be performed after the mixing module 1000 is coupled to the refrigerant providing device 2000.

After the assembly of the mixture spry system 100 is completed, the user may spray the composition and refrigerant to the target.

After the use of the mixture spray system 100 is completed, the user may reverse the assembly process of the mixture spray system 100 described above. For example, a user may separate the mixture spray system 100 into the mixing module 1000 and the refrigerant providing device 2000 and remove the cartridge CTR from the refrigerant providing device 2000.

Meanwhile, a situation in which the cartridge CTR or the mixing module 1000 needs to be replaced may occur during use of the mixture spray system 100. Here, one procedure may be determined based on whether the refrigerant stored in the cartridge CTR is exhausted according to the use of the mixture spray system 100. However, the technical idea of the present disclosure is not limited thereto, and one procedure may be determined based on whether the composition filled in the mixing module 1000 is exhausted.

During use of the mixture spray system 100, a situation may occur in which the composition stored in the mixing module 1000 is exhausted but the refrigerant stored in the cartridge CTR is not exhausted. In this case, the user may additionally fill in the mixing module 1000 with the composition and spray the composition and the refrigerant until the refrigerant stored in the cartridge CTR is exhausted. Alternatively, if the criterion for one procedure is determined whether or not the composition in the mixing module 1000 is all consumed, the user can replace the cartridge CTR after spraying all the refrigerant in the cartridge CTR using the mixture spray system 100.

There may be case in which the procedure treatment method is to sequentially spray the first composition and the second composition having different effects. In this case, the user may fill the first mixing module with the first composition, then combine the refrigerant providing device 1000 to spray the refrigerant and the first composition, and then fill the second mixing module with the second composition, and then combine the refrigerant providing device 1000 to spray the refrigerant and the second composition. In this case, the first part procedure time for spraying the first composition and the second part procedure time for spraying the second composition may be determined based on the procedure time when the refrigerant stored in the cartridge CTR is exhausted. Furthermore, the amount of the first composition filled in the first mixing module may be determined in consideration of the first part procedure time, and the amount of the second composition filled in the second mixing module may be determined in consideration of the second part procedure time.

When performing a new procedure after using the mixture spray system 100, the cartridge (CTR) needs to be replaced. In the case of performing a new procedure, the previously used cartridge (CTR) may be replaced with a new cartridge (CTR) regardless of whether or not the refrigerant remains. This is because the procedure time is determined depending on whether or not the refrigerant is consumed in the cartridge (CTR).

Meanwhile, when replacing the cartridge CTR, the refrigerant remaining in the cartridge CTR needs to be sufficiently removed. For example, as described above, the user may manipulate the refrigerant providing device 2000 to spray the refrigerant until the refrigerant stops being sprayed, and then separate the cartridge CTR from the main body MB. For another example, the user separates the cartridge CTR from the main body MB but keep it from being completely separated, after the refrigerant remaining in the cartridge CTR is sufficiently discharged through the gap formed between the cartridge coupling unit 2500 of the main body MB and the cartridge CTR, the cartridge CTR can be completely separated.

Features, structures, effects, etc. described in the embodiments hereinabove are included in at least one embodiment of the specification, and are not necessarily limited to only one embodiment. Moreover, features, structures, effects, etc. illustrated in each embodiment may be embodiment while being combined or changed with respect to other embodiments by those skilled in the art to which the embodiments belong. Therefore, descriptions related to the combinations and variations should be construed as being included in the scope of the specification.

Hereinabove, although the embodiments have been described, this is only an example and does not limit the technical idea of the specification, and those skilled in the art will appreciate that various modifications, additions and substitutions are possible, without departing from the scope and spirit of the embodiments. In other words, each component specifically shown in the embodiment can be modified and embodied. Furthermore, differences related to the modifications, additions and substitutions should be construed as being included in the scope of the specification defined by the accompanying claims.

The invention claimed is:

1. A module for a composition to be sprayed with a refrigerant, the module comprising:
 a composition storage configured to store the composition;
 a mixer providing a mixing space for the refrigerant and the composition to be mixed therein, the mixer including:
  an inflow hole formed on a first wall of the mixer, the inflow hole configured to receive the composition from the composition storage, and
  an insertion hole formed on a second wall of the mixer, the second wall extending from the first wall in a direction crossing the first wall, the insertion hole configured to receive a refrigerant spray; and
 a tube disposed between and configured to fluidically connect the composition storage and the mixer, the composition configured to:
  flow from the composition storage to the mixing space of the mixer through the tube based on negative air pressure formed, by a flow of the refrigerant generated by the refrigerant spray, at the inflow hole of the mixer, and
  be mixed, in the mixing space of the mixer, with the refrigerant sprayed by the refrigerant spray,
 the mixer further including:
  a guide structure arranged in the mixing space of the mixer, the guide structure configured to receive the composition from the composition storage via the inflow hole and guide the composition to be mixed with the refrigerant therealong, the guide structure at least partially vertically overlapping the tube and the composition storage in a side view,
  the guide structure including a first part, the first part comprising:
   an end positioned adjacent to the inflow hole formed in the first wall of the mixer, and
   a body extending from the end in an inclined manner and configured to guide, along a first surface of the body, at least a portion of the composition received from the composition storage via the inflow hole,
   wherein a radial gap is formed between a second surface of the body and the first wall of the mixer facing the first part of the guide structure, the second surface of the body opposing the first surface of the body,
 wherein the guide structure has a height measured from a virtual plane comprising the inflow hole,
 wherein a center of the insertion hole has a height measured from the virtual plane, and
 wherein the height of the guide structure is greater than or equal to the height of the center of the insertion hole.

2. The module of claim 1,
 wherein the body of the first part has a first angle with respect to the virtual plane, and wherein the first angle is between 10 degrees to 90 degrees.

3. The module of claim 1,
 wherein the guide structure includes a curved part extending from the body of the first part, the curved part comprising an end disposed on an opposite side of the body, and
 wherein the height of the guide structure is defined as a height of the end of the curved part measured from the virtual plane.

4. The module of claim 1,
 wherein the guide structure further includes a contact part in contact with a particular area of the first wall of the mixer.

5. The module of claim 4,
 wherein the contact part has a first groove, and wherein the composition received from the composition storage via the inflow hole is configured to reach the first part through the first groove.

6. The module of claim 1,
 wherein the guide structure further includes a second part, wherein the second part includes:
  an end positioned adjacent to the inflow hole formed in the first wall of the mixer, and
  a body extending from the end of the second part in an inclined manner and configured to guide, along a first surface of the body of the second part, at least a portion of the composition received from the composition storage via the inflow hole, and
 wherein the inflow hole is positioned between the end of the first part and the end of the second part.

7. The module of claim 6,
 wherein the guide structure includes a third part connecting the first part and the second part.

8. The module of claim 7,
 wherein the mixer has a virtual central axis,
 wherein the guide structure is elongated in a direction parallel to the virtual central axis of the mixer, and
 wherein a vent hole is formed on at least one of the first part, or the second part.

9. The module of claim 8,
 wherein the vent hole is positioned between the inflow hole and the insertion hole in a direction parallel to the virtual central axis of the mixer.

10. The module of claim 1,
wherein a height of the first part measured from the virtual plane is smaller than or equal to the height of the center of the insertion hole.

11. The module of claim 1,
wherein a virtual central axis of the mixer is perpendicular to the insertion hole.

12. The module of claim 1,
wherein the mixer has a virtual central axis,
wherein the first part of the guide structure extends from a first end to a second end in a direction parallel to the virtual central axis of the mixer, and
wherein the inflow hole is positioned between the first end and the second end of the first part.

13. The module of claim 1, further comprising:
a coupler extending from the mixer, the coupler including at least one fixing part,
wherein the coupler is configured to be coupled with the refrigerant spray by the at least one fixing part.

14. A device for spraying a composition and a refrigerant, the device comprising:
a cartridge connector configured to receive a cartridge storing the refrigerant;
a valve fluidically connected to the cartridge connector, the valve configured to control a flow of the refrigerant;
a refrigerant spray configured to spray the refrigerant;
a composition storage configured to store the composition;
a mixer providing a mixing space for the refrigerant and the composition to be mixed therein, the mixer including:
an inflow hole formed on a first wall of the mixer, the inflow hole configured to receive the composition from the composition storage, and
an insertion hole formed on a second wall of the mixer, the second wall extending from the first wall in a direction crossing the first wall, the insertion hole configured to receive the refrigerant spray; and
a tube disposed between and configured to fluidically connect the composition storage and the mixer, the composition configured to:
flow from the composition storage to the mixing space of the mixer through the tube based on negative air pressure formed, by a flow of the refrigerant generated by the refrigerant spray, at the inflow hole of the mixer, and
be mixed, in the mixing space of the mixer, with the refrigerant sprayed by the refrigerant spray,
the mixer further including:
a guide structure arranged in the mixing space of the mixer, the guide structure configured to receive the composition from the composition storage via the inflow hole and guide the composition to be mixed with the refrigerant therealong, the guide structure at least partially vertically overlapping the tube and the composition storage in a side view,
the guide structure including a first part, the first part comprising:
an end positioned adjacent to the inflow hole formed in the first wall of the mixer, and
a body extending from the end in an inclined manner and configured to guide, along a first surface of the body, at least a portion of the composition received from the composition storage via the inflow hole,
wherein a radial gap is formed between a second surface of the body and the first wall of the mixer facing the first part of the guide structure, the second surface of the body opposing the first surface of the body,
wherein the guide structure has a height measured from a virtual plane comprising the inflow hole,
wherein a center of the insertion hole has a height measured from the virtual plane, and
wherein the height of the guide structure is greater than or equal to the height of the center of the insertion hole.

15. The device of claim 14, wherein the mixer includes a first coupler and the refrigerant spray includes a second coupler to be coupled with the first coupler, and
wherein the mixer is detachably coupled to the refrigerant spray.

16. The device of claim 14,
wherein the body of the first part has a first angle with respect to the virtual plane, and wherein the first angle is between 10 degrees to 90 degrees.

17. The device of claim 14,
wherein the guide structure includes a curved part extending from the body of the first part, the curved part comprising an end disposed on an opposite side of the body, and wherein the height of the guide structure is defined as a height of the end of the curved part measured from the virtual plane.

18. The device of claim 14,
wherein the guide structure further includes a contact part in contact with a particular area of the first wall of the mixer.

19. The device of claim 18,
wherein the contact part has a first groove, and wherein that the composition received from the composition storage via the inflow hole is configured to reach the first part through the first groove.

20. The device of claim 14,
wherein the guide structure further includes a second part,
wherein the second part includes:
an end positioned adjacent to the inflow hole formed in the first wall of the mixer, and
a body extending from the end of the second part in an inclined manner and configured to guide, along a first surface of the body of the second part, at least a portion of the composition received from the composition storage via the inflow hole, and
wherein the inflow hole is positioned between the end of the first part and the end of the second part.

21. The device of claim 20,
wherein the guide structure includes a third part connecting the first part and the second part.

22. The device of claim 21,
wherein the mixer has a virtual central axis,
wherein the guide structure is elongated in a direction parallel to the virtual central axis of the mixer, and
wherein a vent hole is formed on at least one of the first part, or the second part.

23. The device of claim 22,
wherein the vent hole is positioned between the inflow hole and the insertion hole in a direction parallel to the virtual central axis of the mixer.

* * * * *

UNITED STATES PATENT AND TRADEMARK OFFICE
CERTIFICATE OF CORRECTION

PATENT NO. : 12,208,412 B2
APPLICATION NO. : 18/447195
DATED : January 28, 2025
INVENTOR(S) : Kyungbae Kim It is certified that error appears in the above-identified patent and that said Letters Patent is hereby corrected as shown below:

In the Claims

Column 42, Line 63, Claim 8, delete "first part, or" and insert -- first part or --.

Column 44, Line 36 (approx.), Claim 19, delete "wherein that the composition" and insert -- wherein the composition --.

Column 44, Line 59 (approx.), Claim 22, delete "first part, or" and insert -- first part or --.

Signed and Sealed this
First Day of April, 2025

Coke Morgan Stewart
*Acting Director of the United States Patent and Trademark Office*